US011109782B2

(12) United States Patent
Esenaliev et al.

(10) Patent No.: US 11,109,782 B2
(45) Date of Patent: *Sep. 7, 2021

(54) SYSTEMS AND METHODS FOR MEASURING NEONATAL CEREBRAL OXYGENATION

(71) Applicant: Board of Regents, The University of Texas System, Austin, TX (US)

(72) Inventors: Rinat O. Esenaliev, League City, TX (US); Donald S. Prough, Galveston, TX (US); Yuriy Petrov, Galveston, TX (US); Irene Y. Petrov, Galveston, TX (US); C. Joan Richardson, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 401 days.

This patent is subject to a terminal disclaimer.

(21) Appl. No.: 16/249,180

(22) Filed: Jan. 16, 2019

(65) Prior Publication Data
US 2019/0142316 A1    May 16, 2019

Related U.S. Application Data

(63) Continuation of application No. 15/067,707, filed on Mar. 11, 2016, now Pat. No. 10,226,206.
(Continued)

(51) Int. Cl.
*A61B 5/00* (2006.01)
*A61B 5/145* (2006.01)
*A61B 5/1455* (2006.01)

(52) U.S. Cl.
CPC ........ *A61B 5/14552* (2013.01); *A61B 5/0095* (2013.01); *A61B 5/14542* (2013.01);
(Continued)

(58) Field of Classification Search
CPC ... A61B 5/145; A61B 5/1455; A61B 5/14552; A61B 5/14553; A61B 5/14546; A61B 5/6803; A61B 5/0095
See application file for complete search history.

(56) References Cited

U.S. PATENT DOCUMENTS 4,537,197 A    8/1985  Hulka
5,088,493 A    2/1992  Giannini
(Continued)

FOREIGN PATENT DOCUMENTS

DE    4400674    7/1995

OTHER PUBLICATIONS

Notice of allowance dated Apr. 13, 2016 for U.S. Appl. No. 14/793,969.
(Continued)

*Primary Examiner* — Chu Chuan Liu
(74) *Attorney, Agent, or Firm* — Thomas | Horstemeyer

(57) ABSTRACT

Disclosed herein are systems and methods for monitoring one or more of cerebral oxygenation and total hemoglobin concentration that can be used to perform accurate, noninvasive measurement of cerebral venous blood oxygen saturation (oxygenation) in neonatal patients. A neonatal cerebral oxygenation detection apparatus comprises a wearable support having a light emitter and an acoustic sensor coupled thereto. The wearable support can be secured onto a head of an infant, and the light emitter can be configured to emit a light toward a superior sagittal sinus of the infant's head. The acoustic sensor can be configured to detect acoustic pressure generated by blood in the superior sagittal sinus when the superior sagittal sinus blood absorbs the light. Cerebral oxygenation and/or total hemoglobin concentration can be determined based on the acoustic pressure detected by the acoustic detector.

50 Claims, 14 Drawing Sheets

Related U.S. Application Data

(60) Provisional application No. 62/133,304, filed on Mar. 14, 2015.

(52) U.S. Cl.
CPC ...... *A61B 5/14546* (2013.01); *A61B 5/14553* (2013.01); *A61B 5/6803* (2013.01); *A61B 2503/045* (2013.01)

(56) References Cited

U.S. PATENT DOCUMENTS

| | | | |
|---|---|---|---|
| 5,099,842 | A | 3/1992 | Mannheimer et al. |
| 5,228,440 | A | 7/1993 | Chung et al. |
| 5,348,002 | A | 9/1994 | Caro |
| 5,377,673 | A | 1/1995 | Van Dell et al. |
| 5,823,952 | A | 10/1998 | Levinson et al. |
| 5,840,023 | A | 11/1998 | Oraesky et al. |
| 5,897,503 | A | 4/1999 | Lyon et al. |
| 5,941,821 | A | 8/1999 | Chou |
| 6,049,728 | A | 4/2000 | Chou |
| 6,309,352 | B1 | 10/2001 | Oraevsky et al. |
| 6,381,480 | B1 | 4/2002 | Stoddart et al. |
| 6,463,311 | B1 | 10/2002 | Diab |
| 6,466,806 | B1 | 10/2002 | Geva et al. |
| 6,484,044 | B1 | 11/2002 | Lilienfeld-Toal |
| 6,498,942 | B1 | 12/2002 | Esenaliev et al. |
| 6,553,242 | B1 | 4/2003 | Sarussi |
| 6,567,678 | B1 | 5/2003 | Oosta et al. |
| 6,594,515 | B2 | 7/2003 | Watson |
| 6,725,073 | B1 | 4/2004 | Motamedi et al. |
| 6,751,490 | B2 | 6/2004 | Esenaliev et al. |
| 6,846,288 | B2 | 1/2005 | Nagar et al. |
| 6,904,302 | B2 | 6/2005 | Hirabayashi et al. |
| 7,164,938 | B2 | 1/2007 | Geddes et al. |
| 7,322,972 | B2 | 1/2008 | Viator et al. |
| 7,430,445 | B2 | 9/2008 | Esenaliev et al. |
| 7,515,948 | B1 | 4/2009 | Balberg et al. |
| 7,747,301 | B2 | 6/2010 | Cheng et al. |
| 7,916,283 | B2 | 3/2011 | Fukutani et al. |
| 8,108,022 | B2 | 1/2012 | Balberg et al. |
| 8,121,663 | B2 | 2/2012 | Peyman et al. |
| 8,280,469 | B2 | 10/2012 | Baker, Jr. |
| 8,332,006 | B2 | 12/2012 | Naganuma et al. |
| 8,352,005 | B2 | 1/2013 | Esenaliev et al. |
| 8,423,111 | B2 | 4/2013 | Fujiwara |
| 8,501,099 | B2 | 8/2013 | Viator et al. |
| 8,781,548 | B2 | 7/2014 | Besko et al. |
| 8,852,095 | B2 | 10/2014 | Schlottau et al. |
| 8,864,667 | B2 | 10/2014 | Asao et al. |
| 8,885,155 | B2 | 11/2014 | Li et al. |
| 8,930,145 | B2 | 1/2015 | Li et al. |
| 8,934,953 | B2 | 1/2015 | Carr et al. |
| 2002/0137996 | A1 | 9/2002 | Chung et al. |
| 2006/0100530 | A1 | 5/2006 | Kilot et al. |
| 2006/0173331 | A1 | 8/2006 | Booton et al. |
| 2006/0184042 | A1 | 8/2006 | Wang et al. |
| 2007/0015992 | A1 | 1/2007 | Filkins et al. |
| 2008/0255433 | A1 | 10/2008 | Prough et al. |
| 2009/0069652 | A1 | 3/2009 | Lee et al. |
| 2009/0108205 | A1 | 4/2009 | Duffy et al. |
| 2010/0081904 | A1 | 4/2010 | Medina |
| 2010/0249557 | A1 | 9/2010 | Besko et al. |
| 2011/0118576 | A1 | 5/2011 | Eghtesady et al. |
| 2011/0239766 | A1 | 10/2011 | Nakajima et al. |
| 2013/0112001 | A1 | 5/2013 | Furukawa |
| 2013/0150749 | A1 | 6/2013 | Mclean et al. |
| 2013/0190589 | A1 | 7/2013 | Chen et al. |
| 2013/0324815 | A1 | 12/2013 | Jian et al. |
| 2014/0142404 | A1 | 5/2014 | Wang et al. |
| 2014/0275943 | A1 | 9/2014 | Kang et al. |
| 2014/0343384 | A1 | 11/2014 | Floyd et al. |
| 2014/0378811 | A1 | 12/2014 | Nanaumi |
| 2015/0051473 | A1 | 2/2015 | Huang et al. |
| 2015/0099973 | A1 | 4/2015 | Abe |
| 2016/0007892 | A1 | 1/2016 | Esenaliev et al. |
| 2016/0007895 | A1 | 1/2016 | Esenaliev et al. |
| 2016/0015304 | A1 | 1/2016 | Esenaliev et al. |

OTHER PUBLICATIONS

Al-Aweel, et al. Variations in prevalence of hypotension, hypertension, and vasopressor use in NICUs. J Perinatal. Jul.-Aug. 2001;21(5):272-8.

Bassan. Intracranial hemorrhage in the preterm infant: understanding it, preventing it. Clin Perinatal. Dec. 2009;36(4):737-62, v. doi: 10.1016/j.clp.2009.07.014.

Basu, et al. Cerebral blood flow velocity in early-onset neonatal sepsis and its clinical significance. Eur J Pediatr. Jun. 2012; 171(6):901-9. doi: 10.1007/s00431-0 I 1-1643-y. Epub Jan. 4, 2012.

Benders, et al. Phase-contrast magnetic resonance angiography measurements of global cerebral blood flow in the neonate. Pediatr Res. Jun. 2011;69(6):544-7 doi: 10.1203/PDR.0b013e3182176aab.

Biomedical Photonics Handbook. CRS Press, 2003. 22 pages.

Bode, et al. Age dependence of flow velocities in basal cerebral arteries. Arch Dis Child. Jun. 1988;63(6):606- I I.

Booth, et al. Near-infrared spectroscopy monitoring of cerebral oxygen during assisted ventilation. Surg Neural Int. 2011;2:65. doi: 10.4103/2152-7806.81722. Epub May 28, 2011.

Brecht, et al. In vivo monitoring of blood oxygenation in large veins with a triplewavelength optoacoustic system. Opt Express. Nov. 26, 2007;15(24):16261-9.

Cara Vale, et al. Change in cognitive abilities over time during preschool age in low risk preterm children. Early Hum Dev. Jun. 2012;88(6):363-7. doi: 10.1016/j.earlhumdev.2011.09.011. Epub Nov. 1, 2011.

Deeg, et al. Pulsed Doppler sonographic measurement of normal values for the flow velocities in the intracranial arteries of healthy newborns. Pediatr Radial. 1989;19(2):71-8.

Esenaliev, et al. Axial resolution of laser optoacoustic imaging: Influence of acoustic attenuation and diffraction. SPIE Proc 1998; 3254: 294-301.

Esenaliev, et al. Laser optoacoustic imaging for breast cancer diagnostics: limit of detection and comparison with x-ray and ultrasound imaging. Proc SPIE 1997; 2979: 71-82.

Esenaliev, et al. Optoacoustic technique for noninvasive monitoring of blood oxygenation: a feasibility study. Appl Opt. Aug. 1, 2002;41(22):4722-31.

Esenaliev, et al. Optoacoustic technique for non-invasive, real-time monitoring of cerebral blood oxygenation. LEOS Proc 2001; 192-3.

Esenaliev, et al. Studies of acoustical and shock waves in the pulsed laser ablation of biotissue. Lasers Surg Med. 1993;13(4):470-84.

F Anaroff, et al. Blood pressure disorders in the neonate: hypotension and hypertension. Semin Fetal Neonatal Med. Jun. 2006; I I (3):174-81. Epub Mar. 3, 2006.

Fauchere, et al. Near-infrared spectroscopy measurements of cerebral oxygenation in newborns during immediate postrtatal adaptation. J Pediatr. Mar. 2010;I 56(3):372-6. doi: 10.1016/j.jpeds.2009.09.050. Epub Nov. 14, 2009.

Gilmore, et al. Relationship between cerebrovascular dysautoregulation and arterial blood pressure in the premature infant. J Perinatal. Nov. 2011;3 I ( I I ):722-9. doi: 10.1038/jp.2011.17. Epub Mar. 3, 2011.

Gusev, et al. Laser Optoacoustics. New York, American Institute of Physics Press, 1993. 4 pages.

Heldt, et al. Continuous quantitative monitoring of cerebral oxygen metabolism in neonates by ventilator-gated analysis ofNIRS recordings. Acta Neurochir Suppl. 2012;114:177-80. doi: 10.1007/978-3-7091-0956-4_34.

Honda, et al. Effect of therapeutic touch on brain activation of preterm infants in response to sensory punctate stimulus: a near-infrared spectroscopy-based study. Arch Dis Child Fetal Neonatal Ed. May 2013;98(3):F244-8. doi: 10.1136/archdischild-2011-301469. Epub Jul. 21, 2012.

Iadecola, et al. Glial regulation of the cerebral microvasculature. Nat Neurosci. Nov. 2007;IO(I I ):1369-76.

(56) References Cited

OTHER PUBLICATIONS

International search report and written opinion dated Dec. 8, 2015 for PCT/US2015/03 9620.
Kehrer, et al. Development of cerebral blood flow volume in preterm neonates during the first two weeks of life. Pediatr Res. Nov. 2005;58(5):927-30. Epub Sep. 23, 2005.
Kehrer, et al. Measurement of volume of cerebral blood flow in healthy preterm and term neonates with ultrasound. Lancet. Nov. 30, 2002;360(934 7): 17 49-50.
Kennedy, et al. An adaptation of the nitrous oxide method to the study of the cerebral circulation in children; normal values for cerebral blood flow and cerebral metabolic rate in childhood. J Clin Invest. Jul. 1957;36(7):1130-7.
Kissack, et al. Postrtatal changes in cerebral oxygen extraction in the preterm infant are associated with intraventricular hemorrhage and hemorrhagic parenchymal infarction but not periventricular leukomalacia. Pediatr Res. Jul. 2004;56(1 ): 111-6. Epub May 19, 2004.
Larin, et al. Comparison of Optoacoustic Tomography with Ultrasound and X-ray imaging for Breast Cancer Detection. SPIE Proc. 2001; 4256: 147-53.
Munro, et al. Hypotensive extremely low birth weight infants have reduced cerebral blood flow. Pediatrics. Dec. 2004; 114( 6): 1591-6.
Niwa, et al. Anatomic dependency of phase shifts in the cerebral venous system of neonates at susceptibility-weighted MRI. J Magn Reson Imaging. Nov. 2011;34(5):1031-6. doi: 10.1002/jmri.22782. Epub Aug. 23, 2011.
Noori, et al. Systemic and cerebral hemodynamics during the transitional period after premature birth. Clin Perinatal. Dec. 2009;36(4):723-36, v. doi: 10.1016/j.clp.2009.07.015.
Office action dated Nov. 20, 2015 for U.S. Appl. No. 14/793,969.
Oraevsky, et al. Breast cancer diagnostics by laser opto-acoustic tomography. Advances in Optical Imaging and Photon Migration. Edited by Alfano RR, Fujimoto JG. OSA Publishing House, 1996, pp. 316-321.
Oraevsky, et al. Laser optic-acoustic tomography for medical diagnostics: principles. Proc SPIE 1996; 2676: 22-31.
Oraevsky, et al. Laser-based optoacoustic imaging in biological tissues. Proc SPIE, Laser Tissue Interation V. 1994; 2134: 122-8.
Oraevsky, et al. Two-dimensional opto-acoustic tomography transducer array and image reconstruction algorithm. SPIE Proc 1999; 3601: 256-67.
Patrikeev, et al. Signal processing of optoacoustic transients for monitoring of total hemoglobin concentration and oxygenation in blood vessels. SPIE Photonics West BiOS 2007. Conference 6437. Abstract 6437.43.
Patrikeev, et al. Wavelet differentiation of optoacoustic signals for monitoring of total hemoglobin concentration and oxygen saturation level in small blood vessels. Proc. SPIE 2007; 6437, 643717 (Feb. 13, 2007); doi:10.1117/12.714185.
Petrov, et al. Clinical tests of noninvasive, optoacoustic, cerebral venous oxygenation monitoring system. Photons Plus Ultrasound: Imaging and Sensing 2009, edited by Alexander a Oraevsky, Lihong V. Wang, Proc. ofSPIE vol. 7177, 717706.2009.
Petrov, et al. Monitoring cerebral venous blood oxygentation in neonates with a medical-grade optoacoustic system. Proc. ofSPIE. 2015; vol. 9323:932302. doi: 10.1117 /12.2085076.
Petrov, et al. Multiwavelength optoacoustic system for noninvasive monitoring of cerebral venous oxygenation: a pilot clinical test internal jugular vein. Opt Lett. Jun. 15, 2006;31(12): 1827-9.
Petrov, et al. Noninvasive optoacoustic monitoring of cerebral venous blood oxygenation in newborns. Proc. SPIE 8223, Photons Plus Ultrasound: Imaging and Sensing 2012, 82231M (Feb. 9, 2012).
Petrov, et al. Optoacoustic monitoring of cerebral venous blood oxygenation though intact scalp in large animals. Opt Express. Feb. 13, 2012;20(4):4159-67. doi: 10.1364/OE.20.004159.
Petrov, et al. Optoacoustic, noninvasive, real-time, continuous monitoring of cerebral blood oxygenation: an in vivo study in sheep. Anesthesiology. Jan. 2005; I 02(1):69-75.
Petrov A, et al. Noninvasive monitoring of cerebral blood oxygenation in ovine superior sagittal sinus with novel multi-wavelength optoacoustic system. Opt Express. Apr. 27, 2009;17(9):7285-94.
Pollard, et al. The influence of carbon dioxide and body position on near-infrared spectroscopic assessment of cerebral hemoglobin oxygen saturation. Anesth Analg. Feb. 1996;82(2):278-87.
Pryds, et al. Heterogeneity of cerebral vasoreactivity in preterm infants supported by mechanical ventilation. J Pediatr. Oct. 1989; I I 5(4):638-45.
Reynolds, et al. Spectral pattern of neonatal cerebral blood flow velocity: comparison with spectra from blood pressure and heart rate. Pediatr Res. Feb. 1997;41(2):276-84.
Robertson, et al. Prevention of secondary ischemic insults after severe head injury. Crit Care Med. Oct. 1999;27(10):2086-95.
Roggan, et al. Optical Properties of Circulating Human Blood in the Wavelength Range 400-2500 nm. J Biomed Opt. Jan. 1999;4(1):36-46.
Sorensen, et al. The brains of very preterm newborns in clinically stable condition may be hyperoxygenated. Pediatrics. Nov. 2009; I 24(5):e958-63. doi: 10.1542/peds.2008-2394. Epub Oct. 19, 2009.
Soul, et al. CSF removal in infantile posthemorrhagic hydrocephalus results in significant improvement in cerebral hemodynamics. Pediatr Res. May 2004;55(5):872-6. Epub Jan. 22, 2004.
Soul, et al. Fluctuating pressure-passivity is common in the cerebral circulation of sick premature infants. Pediatr Res. Apr. 2007;61(4):467-73.
Takahashi, et al. Developmental changes of cerebral blood flow and oxygen metabolism in children. AJNR Am J Neuroradiol. May 1999;20(5):917-22.
Tsuji, et al. Cerebral intravascular oxygenation correlates with mean arterial pressure in critically ill premature infants. Pediatrics. Oct. 2000; 106(4) :625-3 2.
Varela, et al. Mean cerebral blood flow measurements using phase contrast MRI in the first year oflife. NMRBiomed. Sep. 2012;25(9):1063-72. doi: 10.1002/nbm.2771. Epub Jan. 31, 2012.
Volpe. Brain injury in premature infants: a complex amalgam of destructive and developmental disturbances. Lancet Neurol. Jan. 2009;8(1):110-24. doi: 10.1016/S I 474-4422(08)70294-1.
Welch, et al. Optical-thermal response of laser-irradiated tissue. New York, Plenum Press, 1995. 13 pages.
Wintermark, et al. Brain perfusion in asphyxiated newborns treated with therapeutic hypothermia. AJNR Am J Neuroradiol. Dec. 2011;32(11):2023-9. doi: 10.3174/ajm.A2708. Epub Oct. 6, 2011.
Wong, et al. Impaired autoregulation in preterm infants identified by using spatially resolved spectroscopy. Pediatrics. Mar. 2008;121(3):e604-I I . doi: 10.1542/peds.2007-1487. Epub Feb. 4, 2008.
Wray, et al. Characterization of the near infrared absorption spectra of cytochrome aa3 and haemoglobin for the non-invasive monitoring of cerebral oxygenation. Biochim Biophys Acta. Mar. 30, 1988;933(1):184-92.
Wynne, et al. Optoacoustic Monitoring of Oxygen Saturation in the Superior Sagittal Sinus of Neonates (Abstract A676). American Society of Anesthesiologists. Oct. 16, 2011.

SYSTEMS AND METHODS FOR MEASURING NEONATAL CEREBRAL OXYGENATION

CROSS-REFERENCE

This application is a continuation of copending U.S. Non-Provisional Application having Ser. No. 15/067,707, entitled, "Systems And Methods For Measuring Neonatal Cerebral Oxygenation," and filed Mar. 11, 2016, which claims the benefit of U.S. Provisional Application No. 62/133,304, filed Mar. 14, 2015 and entitled "Systems and Methods for Measuring Neonatal Cerebral Oxygenation", both of which applications are incorporated herein by reference.

The subject matter of this application is related to the subject matter of the following patents and patent applications: U.S. Pat. No. 6,309,352, issued Oct. 27, 1998 and entitled "Real Time Optoacoustic Monitoring of Changes in Tissue Properties," U.S. Pat. No. 6,498,942, issued Dec. 24, 2002 and entitled "Optoacoustic Monitoring of Blood Oxygenation," U.S. Pat. No. 6,725,073, issued Apr. 20, 2004 and entitled "Methods for Noninvasive Analyte Sensing," U.S. Pat. No. 6,751,490, issued Jun. 15, 2004 and entitled "Continuous Optoacoustic Monitoring of Hemoglobin Concentration and Hematocrit," U.S. Pat. No. 7,430,445, issued Sep. 30, 2008 and entitled "Noninvasive Blood Analysis by Optical Probing of the Veins Under the Tongue," and U.S. Pat. No. 8,352,005, issued Jan. 8, 2013 and entitled "Noninvasive Blood Analysis by Optical Probing of the Veins Under the Tongue," and U.S. patent application Ser. No. 12/101,891, filed Apr. 11, 2007 and entitled "Optoacoustic Monitoring of Multiple Parameters," Ser. No. 14/793,969, filed Jul. 8, 2015 and entitled "Systems and Method for Measuring Fetal Cerebral Oxygenation," Ser. No. 14/794,022, filed Jul. 8, 2015 and entitled "Systems and Method for Measuring Oxygenation," and Ser. No. 14/794,037, filed Jul. 8, 2015 and entitled "Systems and Method for Measuring Oxygenation," the contents of which are fully incorporated herein by reference.

STATEMENT AS TO FEDERALLY SPONSORED RESEARCH

This invention was made with the support of the United States government under grant/contract number 1R41HD076568-01, awarded by the National Institutes of Health (NIH). The government has certain rights in the invention.

BACKGROUND

Cerebral hypoxia is a risk factor for death or severe neurologic complications (e.g., cerebral palsy) for low birth weight neonatal infants. Unfortunately, the ability of the cerebral vasculature of low birth weight neonates to maintain adequate cerebral blood flow is poorly understood. Although clinical studies have been performed with classical Kety-Schmidt methodology, Doppler ultrasound, positron emission tomography, perfusion computed tomography, magnetic resonance imaging and near-infrared (NIR) spectroscopy, there is currently no technique for easily, repeatedly and noninvasively monitoring or measuring cerebral circulatory adequacy in low birth weight infants. NIR spectroscopic techniques that rely on returning or transmitted light have limited ability to separate the signal derived from venous saturation, which reflects tissue oxygen uptake, and arterial saturation, which represents a component of oxygen supply. Moreover, the relative proportions of venous to arterial blood are altered by changes in body position, cerebral venous pressure (CVP), and cerebral vasodilatory stimuli.

In view of the above, it would be desirable to provide systems and methods for continuously monitoring cerebral oxygen in such patients. Ideally, such systems and methods can provide continuous monitoring of cerebral oxygen in the first 48 hours after birth, during which cerebral circulatory function must rapidly adapt to the change from the placental circulation to independent control of blood pressure. Evidence of cerebral ischemia can prompt therapy to increase cerebral blood flow.

References that may be of interest include: U.S. Pat. Nos. 4,537,197, 5,088,493, 5,099,842, 5,228,440, 5,348,002, 5,377,673, 5,823,952, 5,840,023, 5,941,821, 6,049,728, 6,381,480, 6,553,242, 6,594,515, 6,463,311, 6,466,806, 6,484,044, 6,567,678, 6,751,490, 6,846,288, 7,164,938, 7,322,972, 7,515,948, 7,747,301, 7,916,283, 8,121,663, 8,280,469, 8,332,006, 8,423,111, 8,501,099, 8,781,548, 8,852,095, 8,864,667, 8,885,155, 8,930,145, and 8,934,953; U.S. Publication Nos. 2006/100530, 2006/184042, 2007/015992, 2009/069652, 2009/108205, 2010/081904, 2011/239766, 2013/112001, 2013/190589, 2013/324815, 2014/142404, 2014/275943, 2014/343384, 2014/378811, 2015/051473, and 2015/099973; German Patent Publication No. DE 4400674 A1; and, "Noninvasive monitoring of cerebral blood oxygenation in ovine superior sagittal sinus with novel multi-wavelength optoacoustic system" to Petrov et al. (27 Apr. 2009/Vol. 17, No. 9/OPTICS EXPRESS 7285) and "Noninvasive optoacoustic monitoring of cerebral venous blood oxygenation in newborns" to Petrov et al. (Proc. SPIE 8223, Photons Plus Ultrasound: Imaging and Sensing 2012, 82231M (Feb. 9, 2012)).

SUMMARY

Disclosed herein are systems and methods for monitoring cerebral oxygenation that can be used to perform accurate, noninvasive measurement of cerebral venous blood oxygen saturation in neonatal patients. In particular, disclosed herein are systems and methods for providing optoacoustic measurement of the superior sagittal sinus (SSS) of a neonate's head in order to determine cerebral venous oxygen saturation. Such a measurement technique provides high contrast and high resolution that enables direct probing of blood vessels. Because cerebral venous desaturation provides direct evidence that cerebral oxygen availability is insufficient to satisfy cerebral oxygen requirements, decreasing SSS oxygenation (SSS($SO_2$)) can provide an early warning of neonatal cerebral hypoxia.

Aspects of the present disclosure provide neonatal cerebral oxygenation monitoring apparatuses. An exemplary detection apparatus may comprise a wearable support, a light emitter, and an acoustic sensor. The wearable support may be configured to be secured onto a head of an infant. The light emitter may be configured to emit light and coupled to the support such that when the support is secured onto the infant's head, the light can be emitted toward a superior sagittal sinus of the infant's head. The acoustic sensor may be configured to detect acoustic pressure generated by blood in the superior sagittal sinus when the superior sagittal sinus blood absorbs the light signal.

The emitter may be coupled to the support such that the emitter emits the light from a posterior portion of the infant's head when the support is secured onto the infant's head. The emitter may be configured to emit the light toward a posterior fontanelle of the infant's head. Alternatively or in combination, the emitter may be coupled to the support such that the emitter emits the light from a superior portion of the infant's head when the support is secured onto the infant's head. And, the emitter may be configured to emit the light toward an anterior fontanelle of the infant's head. The acoustic sensor may be coupled to the support such that the acoustic sensor detects the acoustic pressure from an anterior portion of the infant's head when the support is secured onto the infant's head.

The apparatus may further comprise a processor configured to determine one or more of venous oxygenation and total hemoglobin concentration in response to the detected acoustic pressure. The apparatus may further comprise a cable coupling the processor to the acoustic sensor. The emitter may comprise a optic waveguide such as fiber optic-based and/or non-fiber waveguides. Alternatively no waveguide(s) can be used and light is delivered through air.

The wearable support may comprise a head band or a head cap. The head cap may comprise a central band adapted to form a continuous loop around the infant's head. The head cap may further comprise a sagittal band extending between front and back sides of the central band to form a path across a top of the infant's head. The head cap may further comprise a web extending upward and rearward from the central band to wrap around a rear of the infant's head above the central band. The head cap may be configured to cover the entirety of the infant's head superior to the central band. The wearable support may comprise a pillow and a headband extending from the pillow.

Aspects of the present disclosure also provide methods for monitoring one or more of cerebral oxygenation or total hemoglobin concentration of an infant. Light may be emitted from a light emitter secured to a head of the infant with a wearable support secured onto the infant's head. The light may be emitted toward a superior sagittal sinus of the infant's head. An acoustic pressure generated by blood in the superior sagittal sinus in response to the emitted light may be detected with an acoustic sensor secured to the infant's head with the wearable support. Cerebral oxygenation and/or total hemoglobin concentration may be determined in response to the detected acoustic pressure.

The light may be emitted from a posterior portion of the infant's head and/or a superior portion of the infant's head. The light signal may be emitted toward a posterior fontanelle of the infant's head and/or an anterior fontanelle of the infant's head. The acoustic pressure may be detected from an anterior portion of the infant's head.

The wearable support may be configured to be secured onto the infant's head. The cerebral oxygenation determined may comprise venous oxygenation.

Aspects of the present disclosure also provide methods for monitoring one or more of cerebral oxygenation or total hemoglobin concentration of an infant. A wearable support may be secured onto a head of the infant. To secure the wearable support, a light emitter coupled to the wearable support may be positioned to a first predetermined position relative to the infant's head and an acoustic sensor coupled to the wearable support may be positioned to a second predetermined position relative to the infant's head. The light emitter may emit light toward a superior sagittal sinus of the infant's head, and the acoustic sensor may detect acoustic pressure generated by blood in the superior sagittal sinus when the superior sagittal sinus blood absorbs the light. Cerebral oxygenation and/or total hemoglobin concentration may be determined in response to the detected acoustic pressure.

The light may be emitted from a posterior portion of the infant's head and/or a superior portion of the infant's head. The light may be emitted toward a posterior fontanelle of the infant's head and/or an anterior fontanelle of the infant's head. The acoustic pressure may be detected from an anterior portion of the infant's head.

The wearable support may be configured to be secured onto the infant's head. The cerebral oxygenation determined may comprise venous oxygenation.

The first predetermined position may be on a first side of the infant's head, and the second predetermined position may be on a second side opposite the first side. Alternatively, the first predetermined position and the second predetermined position are on a same side of the infant's head. And, the first predetermined position may be adjacent the second predetermined position.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. The present disclosure may be better understood with reference to the following figures. Matching reference numerals designate corresponding parts throughout the figures, which are not necessarily drawn to scale. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

As described above, it would be desirable to continuously measure neonatal cerebral oxygenation. Disclosed herein are systems and methods that are well suited for this purpose. In one embodiment, a system for measuring neonatal cerebral oxygenation comprises a light source and an acoustic sensor that are applied to a neonatal infant's head. The light source and acoustic sensor can be held in the correct positions on the head using an apparatus, such as a cap, band, or pillow, specifically designed for that purpose. In some embodiments, the apparatus holds the light source at the rear of the infant's head and holds the acoustic sensor at the front of the infant's head (or vice versa) for transmission mode monitoring. In other embodiments, the apparatus holds the light source and the acoustic sensor at the same point of the infant's head for reflection mode monitoring.

In the following disclosure, various specific embodiments are described. It is to be understood that those embodiments are example implementations of the disclosed inventions and that alternative embodiments are possible. All such embodiments are intended to fall within the scope of this disclosure.

Disclosed herein are systems and methods for monitoring cerebral oxygenation that can be used to perform accurate, noninvasive measurement of cerebral venous blood oxygen saturation in neonatal patients. Cerebral venous oxygen saturation provides in a single number an assessment of the ability of cerebral blood flow and cerebral blood oxygen content to meet cerebral oxygen requirements. As described below, the systems and methods enable optoacoustic measurement in the superior sagittal sinus (SSS). Such a measurement technique provides high contrast and high resolution that enables direct probing of blood vessels. Because cerebral venous desaturation provides direct evidence that cerebral oxygen availability is insufficient to satisfy cerebral oxygen requirements, decreasing SSS oxygenation (SSS ($SO_2$)) can provide an early warning of neonatal cerebral hypoxia. In infants, unlike adults, the sagittal sinus is directly below the scalp either without intervening skull or with thin overlying cranial bones, so relatively low-intensity light penetrates well. Because the generated ultrasound signal returns in a straight line from the SSS, the actual saturation of hemoglobin in the SSS can be accurately determined.

Figure 1:
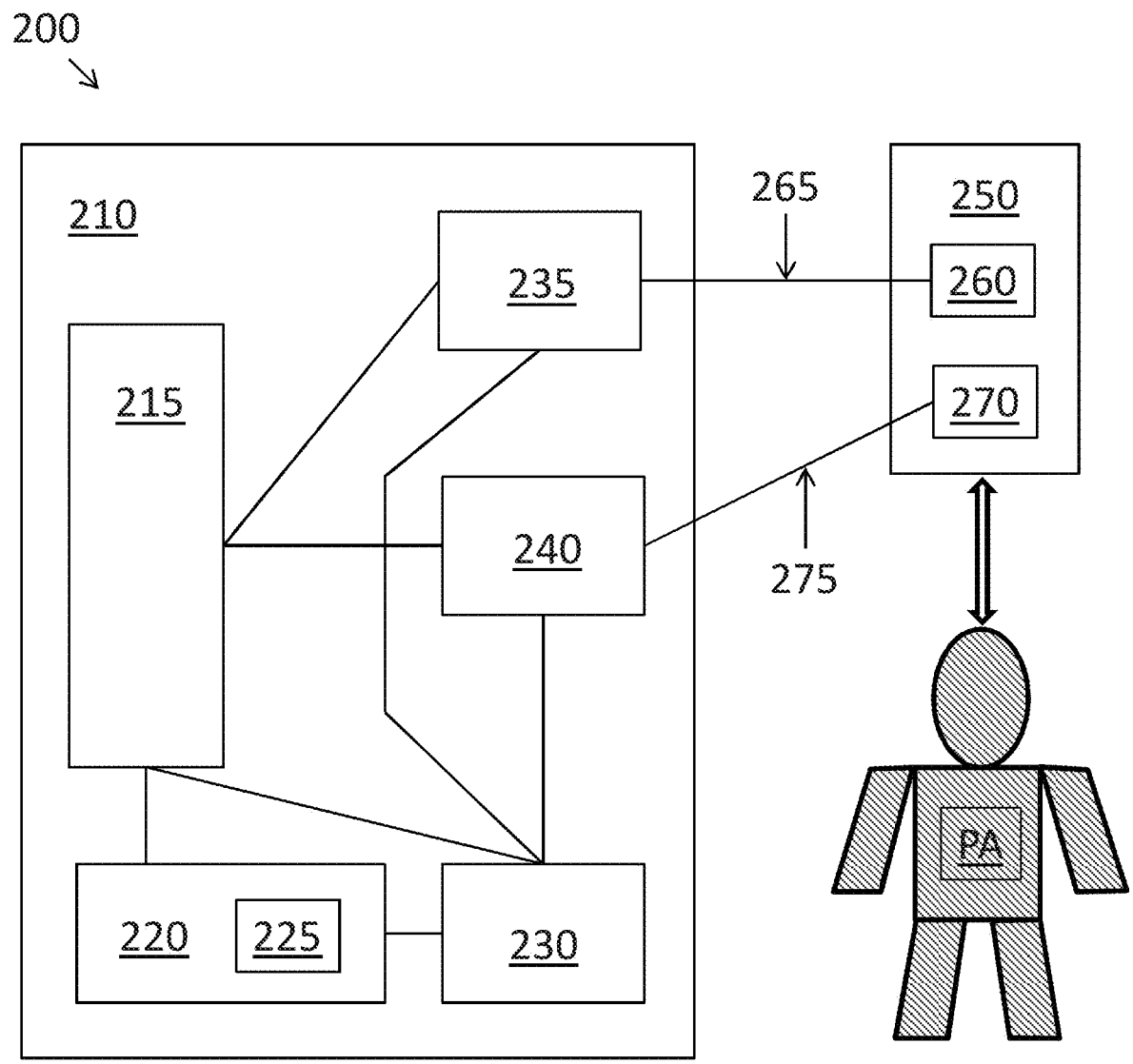
FIG. 1 shows a schematic diagram of a system for optoacoustically measuring cerebral oxygenation of a neonate.

FIG. 1 shows a schematic diagram of a system 200 for optoacoustically measuring cerebral oxygenation (e.g., SSS ($SO_2$)) of a neonate. The system 200 may comprise a console 210 and a patient interface such as a wearable support 250 operatively coupled with one or more wire or cable connections, such as cable 265 and cable 275. The console 210 may comprise a console comprising one or more subsystems or components configured to provide measurement of cerebral oxygenation in a neonatal patient PA via the wearable support 250. The console 210 may comprise a computer board or processor 215, a user interface 220, a power supply subsystem 230, a laser emitter or diode subsystem 235, and an acoustic sensor subsystem 240. The processor 215 may be in communication with the one or more subsystems or components of the console 210, so as to control and monitor the operation of the subsystems. For example, the processor may comprise one or more universal serial bus (USB) ports or other types of data transfer ports configured to connect to the one or more subsystems. The processor 215 may further comprise an audio port to output alarms and message(s) through a speaker. The power supply subsystem 230 may be configured to provide power to one or more components of the system 210, such as the processor, user interface, laser diode subsystem, and acoustic sensor subsystem. The power supply subsystem 230 may be configured to connect to an external AC or DC power source and may comprise a battery to provide back-up power in case of loss of external power.

The wearable support 250 may comprise one or more components configured to be worn securely by the patient during measurement with the system, such as one or more of a head cap, headband, and a pillow as described herein. The wearable support can support a light emitter 260 and an acoustic sensor 270 as described in further detail herein. In particular, the wearable support can be adapted to support the light emitter and the acoustic sensor in particular, pre-determined positions and/or orientations with respect to the patient's head.

The light emitter 260 may be configured to emit light pulses or modulated continuous wave light directed at the target tissue. The light output may output light from a pulsed light source or modulated continuous wave light source. The light source may comprise, for example, a laser, an array of lasers, a light emitting diode (LED), a light emitting diode (LED) array, a pulsed laser diode array configured to generate light pulses or modulated continuous wave light at one or more wavelengths, a flash lamp, a filtered light source, or other light source, to name a few. The light emitter can be connected to the console 210 via a fiber optic cable, for example. The light source may comprise the laser emitter subsystem 235 of the console 210. The acoustic sensor 270 can comprise, for example, a piezoelectric sensor, an acoustic sensor based on optical detection of acoustic waves, or another sensor of acoustic waves, connected to the console via a multiwire shielded cable. The cables 265 and 276 connecting the wearable support 250 and the console 210 may comprise connectors to removably couple the cables to the console.

A user of the system 200, such as medical personnel trained to operate the system, can interact with the system via the user interface 220. The user interface 220 may, for example, comprise a display 225 such as a backlit LCD with a touch screen configured to receive one or more inputs from the user. The user interface 220 may further comprise hardware controls for controlling the operation of the system, such as on/off keys and a stop switch configured to put the system in a "safe" mode, wherein all laser diodes are turned off. The user interface 220 may also comprise an input for data such as patient identification, time, temperature, etc. The processor 215 can receive user input via the user interface 220, and transmit instructions based on the user input to one or more subsystems, such as the laser emitter subsystem 235, acoustic sensor subsystem 240, and/or power supply subsystem 230. Based on instructions received from the processor 215, the laser emitter subsystem 235 may generate and emit light pulses which may be directed to a target tissue of the patient PA through the wearable support 250. The light pulses can be conducted through the cable connection 265, such as a fiber optic cable and/or a multiwire shielded cable, to the wearable support 250. For example, the light pulses can be transmitted to the light emitter 260 that is in contact with the target tissue, such as the superior sagittal sinus (SSS). The light pulses can pass through the tissue and bone to the venous blood, wherein absorption of the light pulses can result in the generation of acoustic pressure. The wearable support 250 can detect the acoustic pressure from the target tissue and transmit the acoustic signals back to the console 210, for example via the cable connection 275 to the acoustic sensor subsystem 240. The wearable support 250 can comprise, for example, the acoustic sensor 270 such as a wide-band ultrasound transducer, configured to detect and digitize the acoustic pressure. The acoustic sensor subsystem 240 can receive and/or at least partially process the measured acoustic pressure signals, then digitize the signals, and transmit the signals to the processor 215 for further processing and analysis. The processor 215 can, for example, compute the venous oxygen saturation from the measured acoustic pressure, and transmit results of the measurement to the user interface 220 to be displayed to the user via the display 225. The display 225 may be configured to display oxygen saturation readings (e.g., venous oxygen saturation readings) or other physiological parameters continuously, with updates once per minute, for example. In some embodiments, the system 200 may further comprise a communications subsystem to communicate with other electronic or computerized healthcare management systems. For example, the physiological parameter data measured may be stored and archived (to generate electronic medical records) and analyzed with another computerized system in communication with the system 200.

The system 200 may be configured to have a compact size to accommodate limited spaces available in transport vehicles, forward aid stations, or intensive care units. For example, the console 210 may be desktop-sized. Components of the system 200 may be ergonomically designed so as to allow easy operation for medical personnel who may be generally unfamiliar with opto-acoustic measurements. The display 225 of the system 200 can provide user guidance for use of the system 200, as well as display the status of various alarms of the system 200, in order to help users understand causes of the alarms and take appropriate remedial actions. The system 200 may be configured to allow up to about 24 hours (or more) of continuous monitoring without changing locations, for example. A power loss alarm may be implemented with the system 200, in order to alert the user of signal loss or cable disconnection during monitoring. The system 200 may further be configured to have a user-selectable transport mode that can support battery-operated use of the system 200 for up to about one hour. In the transport mode, the system 200 may be configured to operate with low power (e.g., lower power than in the operational mode), and the power loss alarm may be disabled. The system 200 may be further configured to allow users to input patient identification data, access patient medical records, and download the measurement data collected during the monitoring process for archival and evaluation purposes, for example through the communications subsystem described above.

The system 200 may be configured to monitor various physiological parameters. In many embodiments, oxygen saturation is measured. For example, venous oxygen saturation in the range from about 20% to about 100% (calculated as oxyhemoglobin±total hemoglobin concentration [THb], as described further herein) may be measured. The system 200 may have an accuracy of about +/−3% over the saturation range from about 40% to about 90%, for example.

The acoustic sensor subsystem 240 may receive acoustic signals from the acoustic sensor 270 of the wearable support 250. The acoustic sensor subsystem 240 may comprise a one or more signal amplifiers configured to provide a gain for the received signals. The gain may be, for example, about 40 dB of gain at 500 kHz and may have, for example a −3 dB bandwidth of 50 kHz to 3.5 MHz. The acoustic sensor subsystem 240 may comprise a high speed digitizer that may sample the amplified acoustic signal from the amplifier. This sampling may be performed at a minimum rate 20 MHz, for example. The digitizer may receive a trigger signal from the laser emitter subsystem 235 and store samples, such as a 100, 200, 300, 400, 500, 600, 700, 800, 900, or 1000 samples, of the acoustic signal. The digitizer may transfer the block of samples to the processor 215 for waveform averaging. Often, the acoustic signals generated by the target tissue is low level and averaging readings over hundreds of repetitive cycles can extract the waveform out of background noise.

Described below are embodiments of systems for measuring neonatal cerebral oxygenation that can be used to continuously monitor neonatal SSS(SO$_2$) in a continuous fashion. FIGS. 2-5 are systems that monitor SSS(SO$_2$) in a transmission mode while FIGS. 6 and 7 illustrate systems that monitor SSS(SO$_2$) in a reflection mode.

Figure 2A:
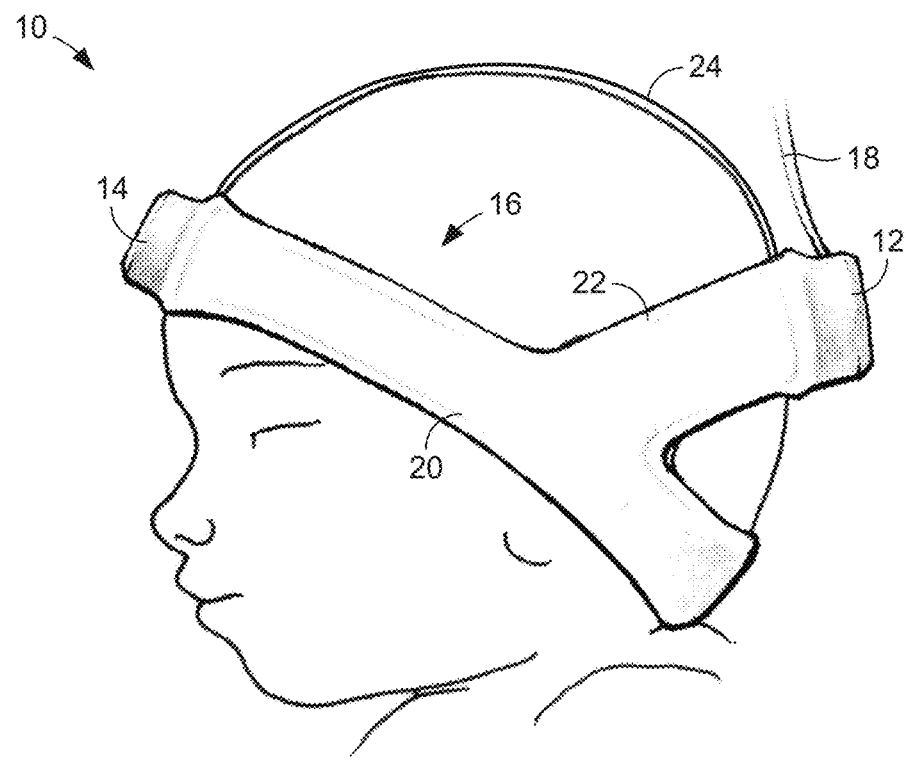
FIGS. 2A and 2B show a system for measuring neonatal cerebral oxygenation, according to many embodiments.
Figure 2B:
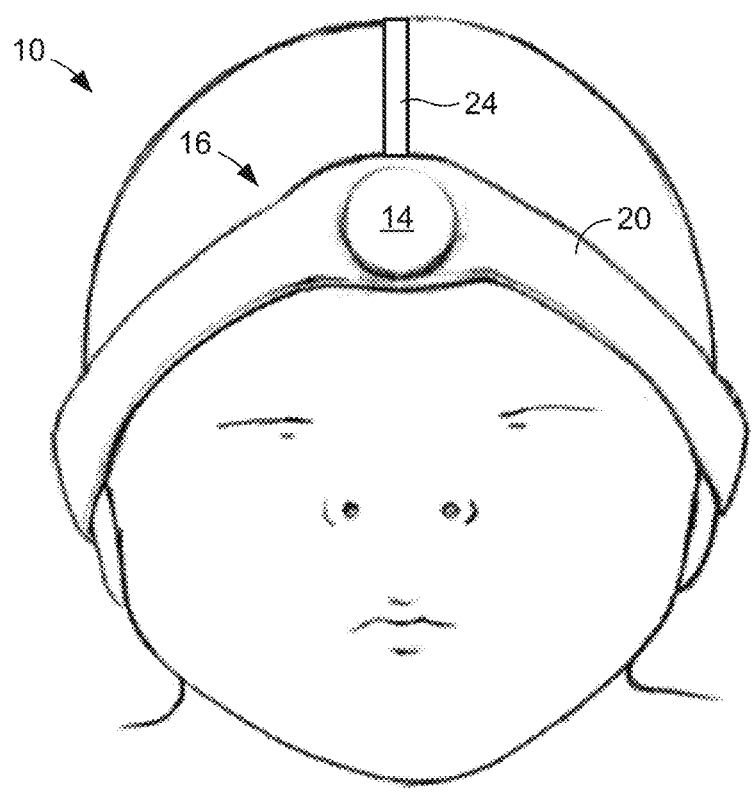

FIGS. 2A and 2B illustrate a first embodiment of a system 10 for measuring neonatal cerebral oxygenation. As indicated in the figure, the system 10 generally comprises a light emitter 12, an acoustic sensor 14, and a head cap 16 that supports the light emitter and acoustic sensor in desired positioned relative to the infant's head. The system 10 may be a portion of the optoacoustic monitoring system 200 as shown in FIG. 10, wherein light emitter 12 corresponds to light emitter 260, acoustic sensor 14 corresponds to acoustic sensor 270, and head cap 16 corresponds to wearable support 250.

The light emitter 12 is configured to emit light, such as near infrared (NIR) laser light, that is generated by a light source, such as a laser (not shown). The light from the source can be provided to the light emitter 12 using a cable 18 that contains an optic waveguide (fiber-based or non-fiber-based) and one or more electrical wires. Because the light emitter 12 contacts the infant's head, the emitted light is transmitted into the head and the tissues within the brain. The absorption of the light's energy in a medium is followed by thermal expansion of the irradiated medium, in this case the SSS, which induces mechanical stress that propagates in the form of acoustic (e.g., ultrasonic) pressure waves. These waves travel through the brain tissue with minimal scattering and can be transmitted to and detected by the acoustic sensor 14, which converts the waves into electrical signals that can be provided to a computer (not shown) for processing.

In some embodiments, the light emitter 12 comprises a housing that at least partially encloses the distal portion of the cable 18 that connects to the light emitter. At least one optical fiber of the fiber optic waveguide may be configured to protrude distally through the housing, in order to minimize optical energy losses in the hair of the subject. When the light emitter is placed against the head of the subject, the protruding fiber can reach the scalp surface through hair to establish direct contact with the scalp. The direct contact between the fiber and the scalp can help reduce energy loss associated with absorption by hair, thereby resulting in better delivery of light to the SSS.

In some embodiments, the fiber optic waveguide of the cable 18 comprises a plurality of optical fibers, wherein each of the plurality of fibers is irradiated sequentially. For example, one fiber may be aligned directly above the SSS, such that the SSS can be illuminated with high specificity while minimizing the influence of signals from non-SSS areas.

In some embodiments, the emitted light is within the low end of the NIR spectral range, such as approximately 600 to 1300 nm. Light in such a wavelength range has deep penetration in tissues, which is sufficient for optoacoustic monitoring of hemoglobin saturation. The amount of laser energy applied for monitoring is small and cannot induce any thermal or mechanical damage to a patient's skin or a patient's or operator's ocular tissues because laser fluence levels are well below the maximum permissible exposures (MPE) for ocular tissues. In some embodiments, the laser energy is delivered at a power of approximately 1 µJ to 1 mJ.

Oxyhemoglobin and deoxyhemoglobin have high absorption coefficients in the visible and NIR spectral range. Therefore, both the amplitude and spatial distribution of the generated optoacoustic pressure induced in blood are dependent on total hemoglobin concentration [THb] and hemoglobin saturation (calculated as oxyhemoglobin [THb]). The high resolution of the disclosed measurement technique enables direct measurement of [THb] and saturation in large blood vessels. In some embodiments, saturation can be assessed using an optical parametric oscillator (OPO) pumped by Nd-YAG laser to generate four important wavelengths: 800 nm (isosbestic point where oxy- and deoxyhemoglobin have equal absorption) and 700, 730, and 760 nm, which are wavelengths at which oxy- and deoxyhemoglobin have strong differences in absorption.

Laser optoacoustic imaging techniques combine the merits of optical tomography (high optical contrast) and ultrasound imaging (minimal scattering of acoustic waves) to yield a noninvasive diagnostic modality with high contrast, sensitivity, and resolution. The high resolution, sensitivity, and contrast of optoacoustic techniques provide monitoring of [THb], oxygenated and deoxygenated hemoglobin with excellent accuracy, specificity and sensitivity. Transmission of ultrasound signals in a straight line differentiates optoacoustic measurements from pure optical techniques in which both incident and returning optical signals are scattered by passage through tissue. Optoacoustic imaging can visualize structures in optically turbid and opaque tissues at depths as great as several centimeters with a spatial resolution ≤0.5 mm and can reconstruct optoacoustic images. In summary, the merits of optoacoustic monitoring include: (1) noninvasiveness, (2) accurate, quantitative measurements, (3) continuous, real-time monitoring, (4) high spatial resolution, and (5) compact dimensions.

As mentioned above, the acoustic sensor 14 detects the ultrasonic waves that are generated by the SSS of the neonate. In some embodiments, the acoustic sensor 14 comprises a piezoelectric transducer that uses the piezoelectric effect to measure changes in pressure, acceleration, strain, or force and convert them into an electrical signal. The electrical signals generated by the acoustic sensor 14 can be transmitted to another device, such as a computer, using one or more electrical wires that extend through the cable 18.

As mentioned above, the head cap 16 is adapted to support the light emitter 12 and acoustic sensor 14 in desired locations on the infant's head to facilitate optoacoustic imaging. In the illustrated embodiment, the light emitter 12 is positioned at the rear (e.g., occipital region) of the infant's head and the acoustic sensor 14 is positioned at the front (e.g., forehead) of the infant's head. With such a configuration, transmission mode optoacoustic imaging can be performed. While the light emitter 12 and the acoustic sensor 14 may not be in direct alignment with each other, the ultrasound signals radiate in all directions within the brain and therefore can be adequately detected by the acoustic sensor.

The light emitter 12 may be positioned near the posterior fontanelle of the infant's head, or at the inion region to target the SSS or the confluence of the sinuses. In some cases, targeting the confluence of sinuses may be preferable as the confluence of sinuses represents a larger optoacoustic source compared to the SSS.

As shown in FIGS. 2A and 2B, the head cap 16 generally comprises a narrow central band 20 that forms a continuous loop adapted to wrap around the head like an conventional headband (from the forehead, over the ears, and to the base of the skull) and a narrow auxiliary band 22 that extends upward and rearward from the central band so as to wrap around the rear of the head above the central band. In the illustrated embodiment, the auxiliary band 22 extends upward and rearward at an angle of approximately 30° to 60° (e.g., 45°) relative to the central band 20 (see FIG. 2A). The acoustic sensor 14 is securely mounted to a front end of the central band 20 in a manner in which the sensor makes contact with the front of the head. The light emitter 12, on the other hand, is securely mounted to the middle of the auxiliary band 22 in a manner in which the emitter makes contact with the rear of the head. The head cap 16 is made of one or more pieces of soft fabric that is comfortable even if worn for extended periods of time. The fabric can comprise natural or synthetic fibers, or a blend of the two. By way of example, the fabric can comprise a fabric blend. In some embodiments, the head cap 16 further includes elastic fibers or an elastic material that enables a snug fit on the head so prevent undesired movement of the light emitter 12 and/or acoustic sensor 14.

As is further shown in FIGS. 2A and 2B, the cap 16 can further include a sagittal band 24 that extends from the front of the central band 20 to center of the auxiliary band 22 and the rear of the central band along a path across the top of the head from front to back (i.e., in the sagittal plane). The sagittal band 24 can be used to adjust the fit of the cap 16 on the head to ensure the light emitter 12 and acoustic sensor 14 are in the correct positions. In some embodiments, the sagittal band 24 can be elastic.

Figure 3A:
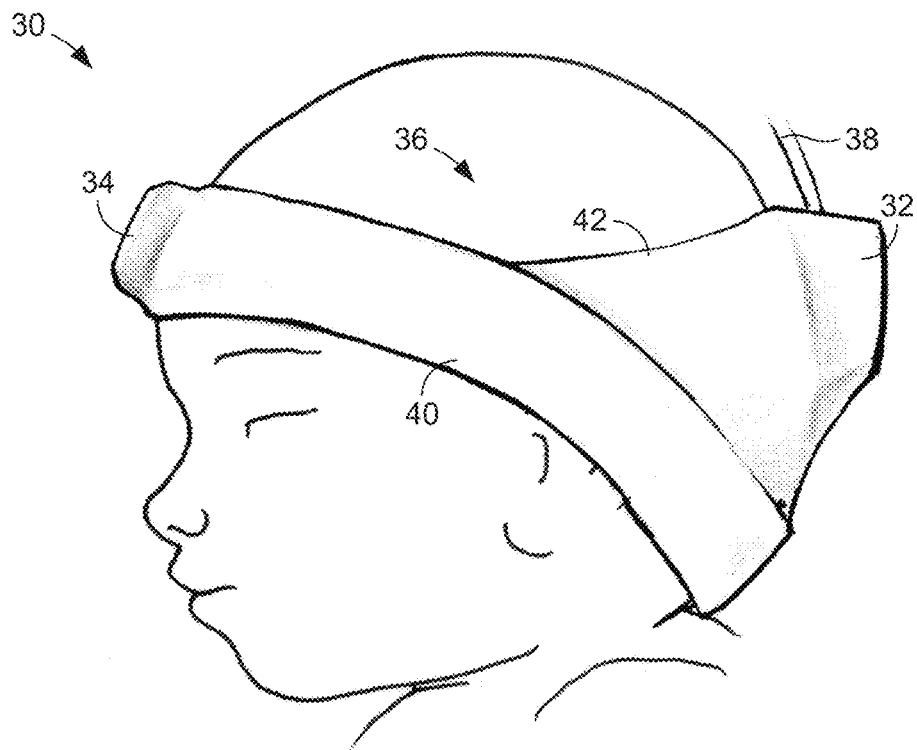
FIGS. 3A and 3B show a system for measuring neonatal cerebral oxygenation, according to many embodiments.
Figure 3B:
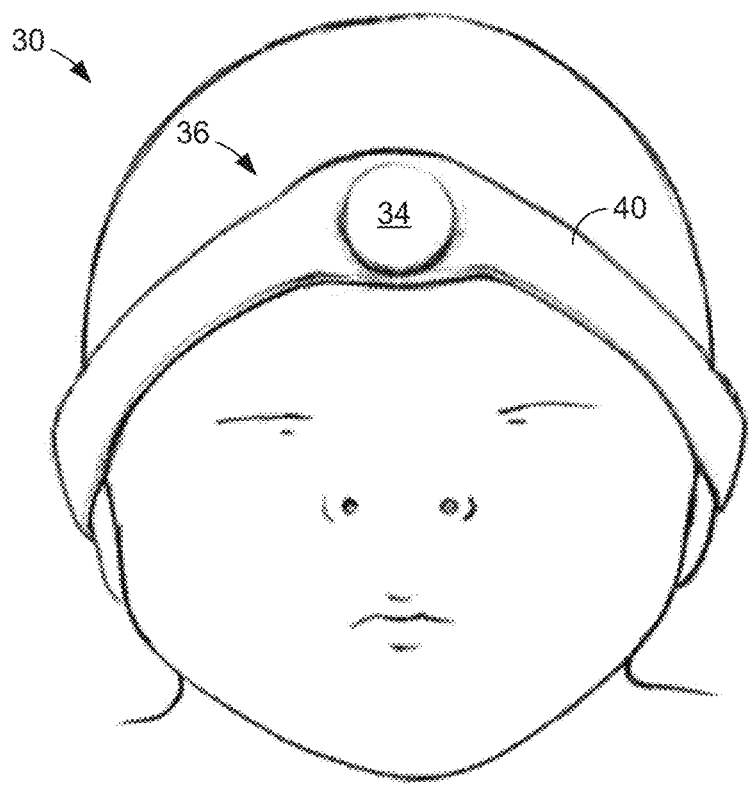

FIGS. 3A and 3B show a further embodiment of a system 30 for measuring neonatal cerebral oxygenation that can be used to continuously monitor neonatal $SSS(SO_2)$. As indicated in these figures, the system 30 also generally comprises a light emitter 32, an acoustic sensor 34, a head cap 36, and a cable 38. The light emitter 32, acoustic sensor 34, and cable 38 can each be configured in the same manner as the like-named components described above in relation to FIGS. 2A and 2B. The head cap 36, however, has a different construction. Like the head cap 16, the head cap 36 comprises a central band 20 that forms a continuous loop adapted to wrap around the head like a conventional headband. However, instead of a narrow auxiliary band that extends upward and rearward from the central band, the cap includes a rear web 42 that extends upward from the rear of the central band so as to cover the entire rear portion of the head above the central band. As with the previous embodiment, the acoustic sensor 34 is securely mounted to a front end of the central band 40 in a manner in which the sensor makes contact with the front of the head. The light emitter 12, however, is securely mounted to an upper portion of the web 42 in a manner in which the emitter makes contact with the rear of the head. The cap 36 can be made from materials similar to those described above in relation to FIGS. 2A and 2B. Accordingly, the cap 36 can comprise natural and/or synthetic fibers and may or may not be elastic. Notably, the cap 36 can include a sagittal band like the cap 16.

Figure 4A:
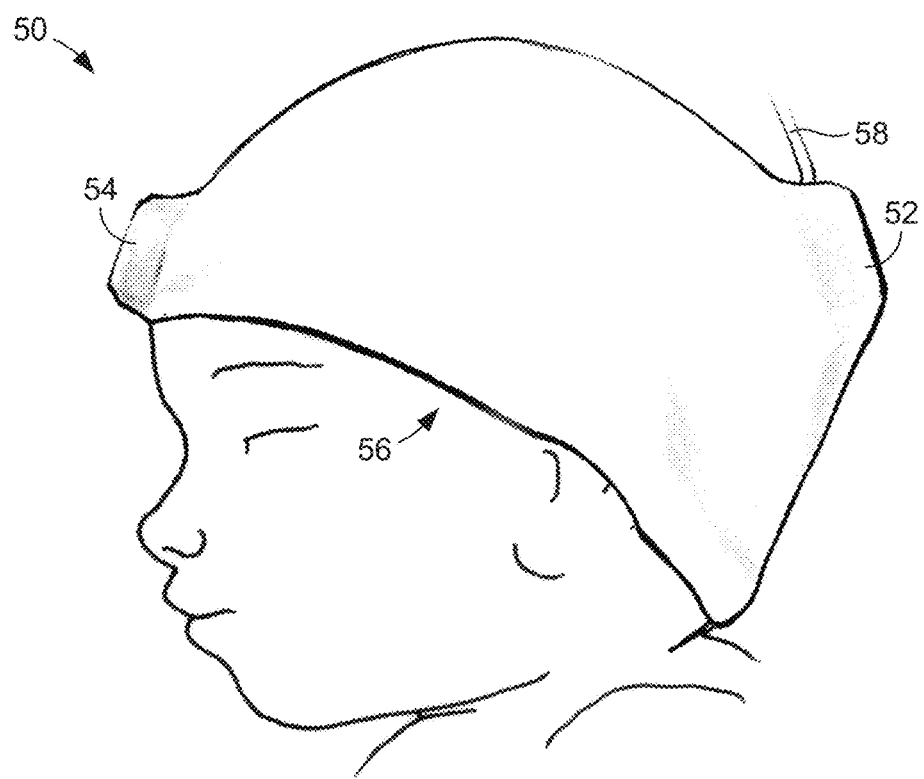
FIGS. 4A and 4B show a system for measuring neonatal cerebral oxygenation, according to many embodiments.
Figure 4B:
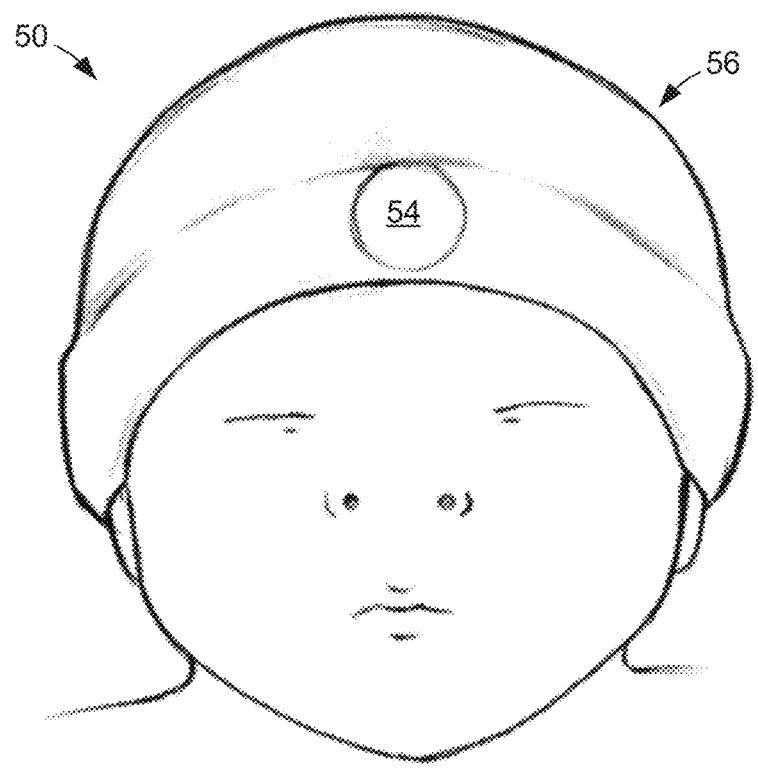

FIGS. 4A and 4B show another embodiment of a system 50 for measuring neonatal cerebral oxygenation that can be used to continuously monitor neonatal $SSS(SO_2)$. As indicated in these figures, the system 50 also generally comprises a light emitter 52, an acoustic sensor 54, a head cap 56, and a cable 38. The light emitter 52, acoustic sensor 54, and cable 58 can each be configured in the same manner as the like-named components described above in relation to FIGS. 2A and 2B. The head cap 36, however, has a different construction. In this embodiment, the cap 56 comprises a continuous cap that covers the entire head in similar manner to a winter cap. The light emitter 52, is securely mounted to a rear upper portion of the cap 56 in a manner in which the emitter makes contact with the rear of the head, while the acoustic sensor 54 is securely mounted to a front lower portion of the cap in a manner in which the sensor makes contact with the front of the head. The cap 36 can be made from materials similar to those described above in relation to FIGS. 2A and 2B. Accordingly, the cap 56 can comprise natural and/or synthetic fibers and may or may not be elastic.

Figure 5A:
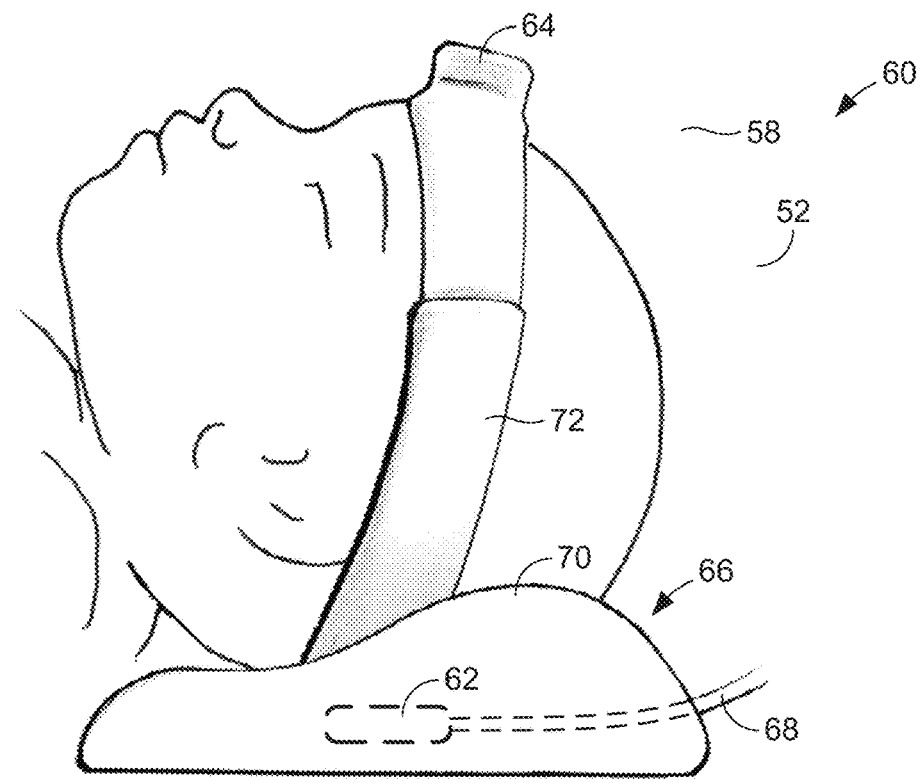
FIGS. 5A and 5B show a system for measuring neonatal cerebral oxygenation, according to many embodiments.
Figure 5B:
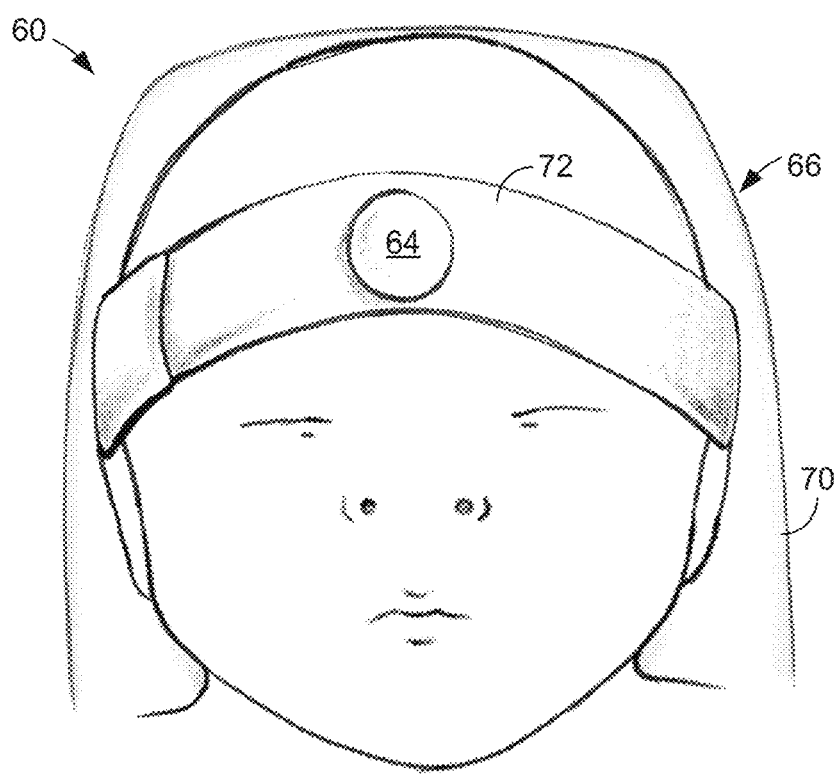

FIGS. 5A and 5B show yet another embodiment of a system 60 for measuring neonatal cerebral oxygenation that can be used to continuously monitor neonatal $SSS(SO_2)$. As indicated in these figures, the system 50 also generally comprises a light emitter 62, an acoustic sensor 64, an apparatus 66 for supporting the emitter and sensor, and a cable 68. The light emitter 52, acoustic sensor 54, and cable 58 can each be configured in the same manner as the like-named components described above in relation to FIGS. 2A and 2B. The apparatus 66, however, does not comprise a head cap. Instead, the apparatus 66 comprises a pillow 70 from which extends a headband 72. As shown in FIG. 5A, the light emitter 62 is mounted on or in the pillow 70 so that it makes contact with the rear of the infant's head when the head is laid upon the pillow while the infant is on its back. The acoustic sensor 64 is securely mounted to a front end of the headband 72 in a manner in which the sensor makes contact with the front of the head.

The apparatus 66 can also be made from materials similar to those described above in relation to FIGS. 2A and 2B. Accordingly, the pillow 70 and/or headband 72 can comprise natural and/or synthetic fibers and may or may not be elastic. The pillow 70 can also comprise natural and/or synthetic cushion material that supports the infant's head.

Each of the above-described embodiments operate in a transmission mode in which acoustic pressure waves travel to an acoustic sensor that is positioned on an opposite side of the infant's head from where the light emitter is located. It is noted that a reflective mode can be used in which both the acoustic sensor and the light emitter are located on the same side, and even at the same point, of the infant's head. FIGS. 6 and 7 illustrate examples of such embodiments.

Figure 6A:
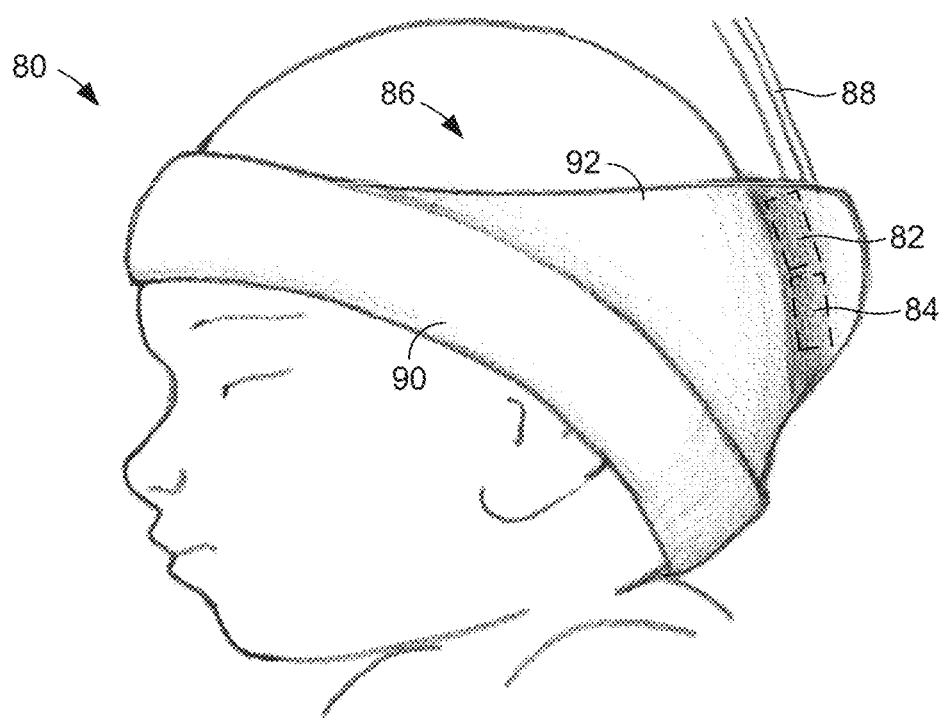
FIGS. 6A and 6B show a system for measuring neonatal cerebral oxygenation, according to many embodiments.
Figure 6B:
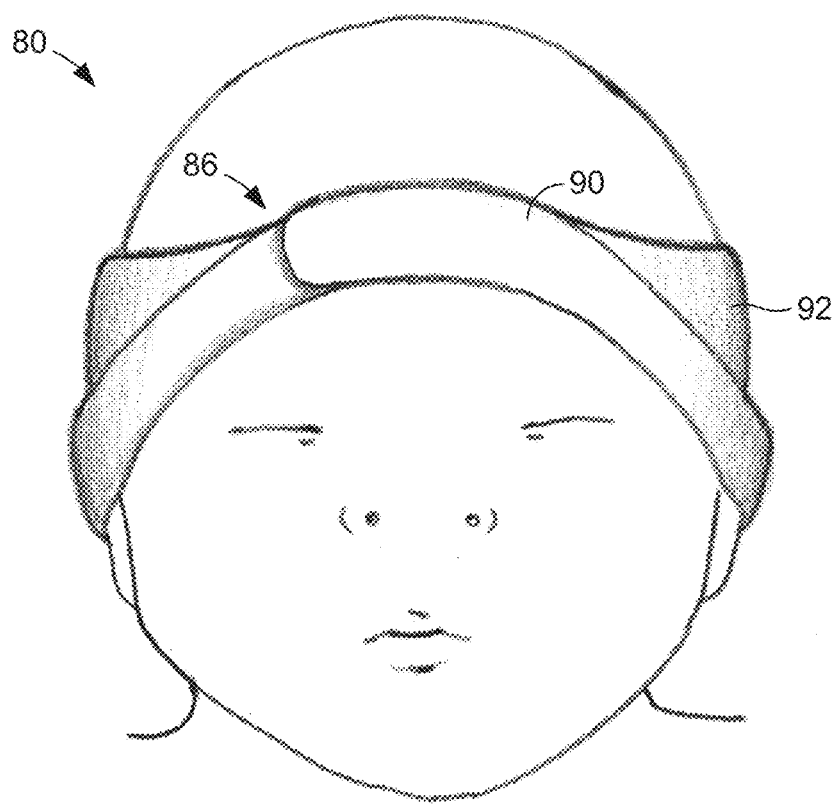

FIGS. 6A and 6B show an embodiment of a system 80 for measuring neonatal cerebral oxygenation that can be used to continuously monitor neonatal $SSS(SO_2)$. As indicated in these figures, the system 80 is very similar to the system 30 shown in FIG. 3. Accordingly, the system 80 generally comprises a light emitter 82, an acoustic sensor 84, a head cap 86, and a cable 88. The head cap 86 comprises a central band 90 that forms a continuous loop adapted to wrap around the head like a conventional headband and a rear web 92 that extends upward from the rear of the central band so as to cover the entire rear portion of the head above the central band. Unlike the system 30, however, both the light emitter 82 and the acoustic sensor 84 are mounted to an upper portion of the web 92. For example, as shown, both the light emitter and the acoustic sensor can be positioned at a posterior portion of the infant's head, such as near the posterior fontanelle of the infant's head. The cap 86 can be made from materials similar to those described above. Accordingly, the cap 86 can comprise natural and/or synthetic fibers and may or may not be elastic.

Figure 7A:
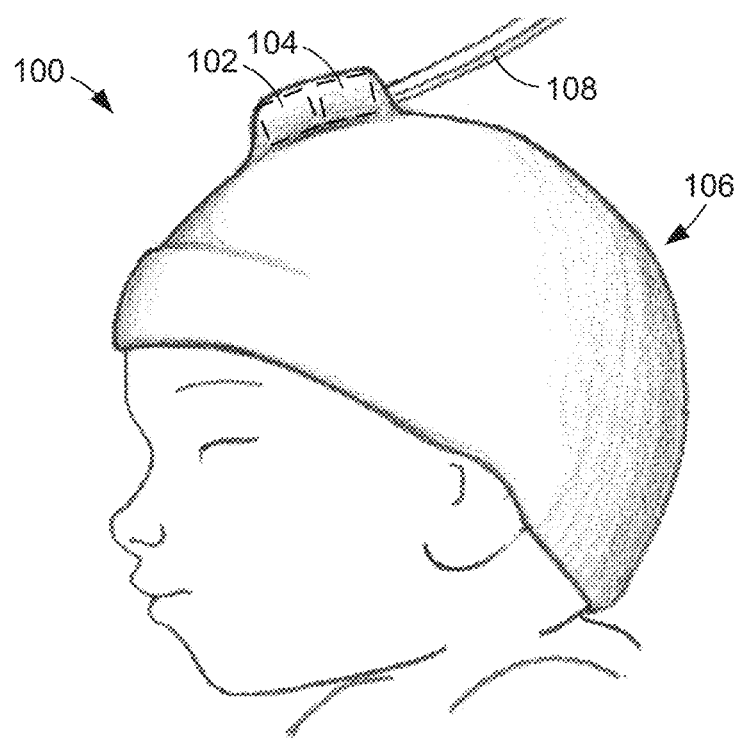
FIGS. 7A and 7B show a system for measuring neonatal cerebral oxygenation, according to many embodiments.
Figure 7B:
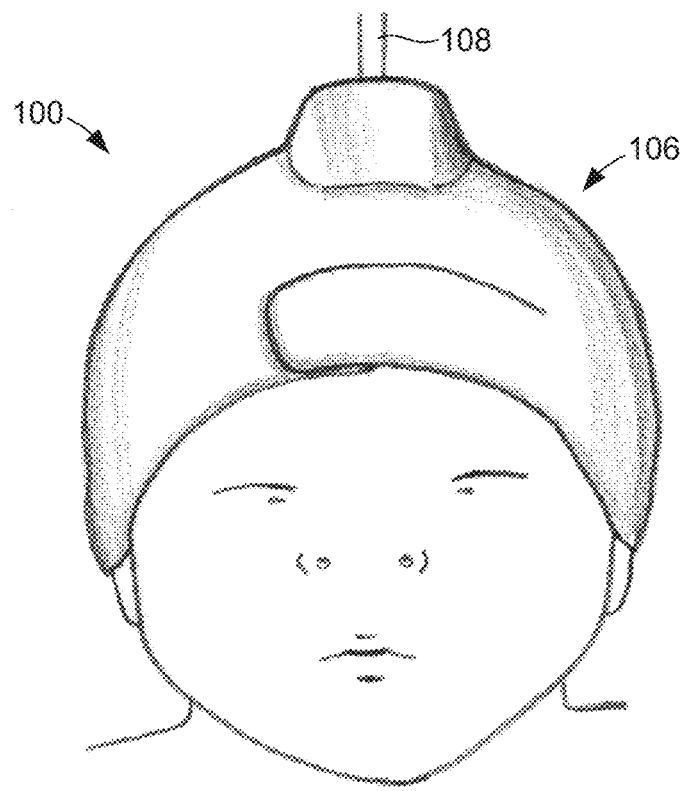

FIGS. 7A and 7B show a further embodiment of a system 100 for measuring neonatal cerebral oxygenation that can be used to continuously monitor neonatal $SSS(SO_2)$. As indicated in these figures, the system 100 is very similar to the system 50 shown in FIG. 4. Accordingly, the system 100 generally comprises a light emitter 102, an acoustic sensor 104, a head cap 106, and a cable 108. The head cap 106 comprises a continuous cap that covers the entire head in similar manner to a winter cap. Both the light emitter 102 and the acoustic sensor 104 are mounted to a front upper portion of the cap 106 near the anterior fontanelle of the infant's head where there is little bone to attenuate the light or acoustic pressure waves. The cap 106 can be made from materials similar to those described above. Accordingly, the cap 106 can comprise natural and/or synthetic fibers and may or may not be elastic.

In any embodiment of a monitoring system as described herein, a processor may be communicatively coupled with the acoustic detector to receive and process the detected signals. For example, the processor may be configured with instructions to determine total hemoglobin concentration [THb] and hemoglobin saturation (calculated as oxyhemoglobin concentration ([oxyHb]÷[THb])) based on the detected signals, wherein the detected signals comprise the amplitude and temporal profile of the optoacoustic pressure waves induced by the irradiation of the target medium. As described herein, the absorption of light energy is followed by thermal expansion of the medium (such as the SSS), which in turn induces mechanical stress that propagates in the form of acoustic pressure waves. The pressure rise, P(z), in a medium induced by a short optical pulse with the incident fluence $F_0$ upon condition of stress confinement can be modeled as follows:

$$P(z) = \beta c_s^2/C_p)\mu_a F = \Gamma \mu F(z) = \Gamma \mu_a F_o \exp(-\mu_a z) \quad \text{(Eq. 1)}$$

wherein β[1/° C.] is the thermal expansion coefficient; $c_s$ [cm/s] is the speed of sound; $C_p$ [J/g° C.] is the heat capacity at constant pressure; F(z) [J/cm²] is the fluence of the optical pulse; and $\mu_a$ [cm⁻¹] is the absorption coefficient of the medium. The optoacoustic pressure in Eq. 1 can be expressed in J/cm³ or in bar (1 J/cm³=10 bar). The expression ($\beta c_s^2/C_p$) in Eq. 1 represents the dimensionless Grüneisen parameter, Γ. The exponential attenuation of the optical radiation in the medium is represented by exp(−$\mu_a$z). Recording and analyzing the amplitude and temporal profile of optoacoustic waves permits calculation of the absorption coefficient of the irradiated medium.

Most tissues are strongly scattering media in the visible and NIR spectral range. Three major optical parameters are responsible for distribution of light in tissues: the absorption coefficient ($\mu_a$), scattering coefficient ($\mu_s$), and effective attenuation coefficient ($\mu_{eff}$). The effective attenuation coefficient is related to $\mu_a$, $\mu_s$, and the anisotropy factor (g) thusly:

$$\mu_{eff} = \{3\mu_a[\mu_a+\mu_s(1-g)]\}^{1/2} \quad \text{(Eq. 2)}$$

wherein $\mu_s$ (1−g) is the reduced scattering coefficient, $\mu_s'$. Light penetration depth in tissues is defined as $1/\mu_{eff}$.

As described herein, oxyhemoglobin (oxyHb) and deoxyhemoglobin (deoxyHb) have high absorption coefficients in the visible and NIR spectral range. Therefore, based on Equations 1 and 2, the measured amplitude and spatial distribution of optoacoustic pressure induced by irradiation can be used to calculate total hemoglobin concentration and saturation.

Figure 8:
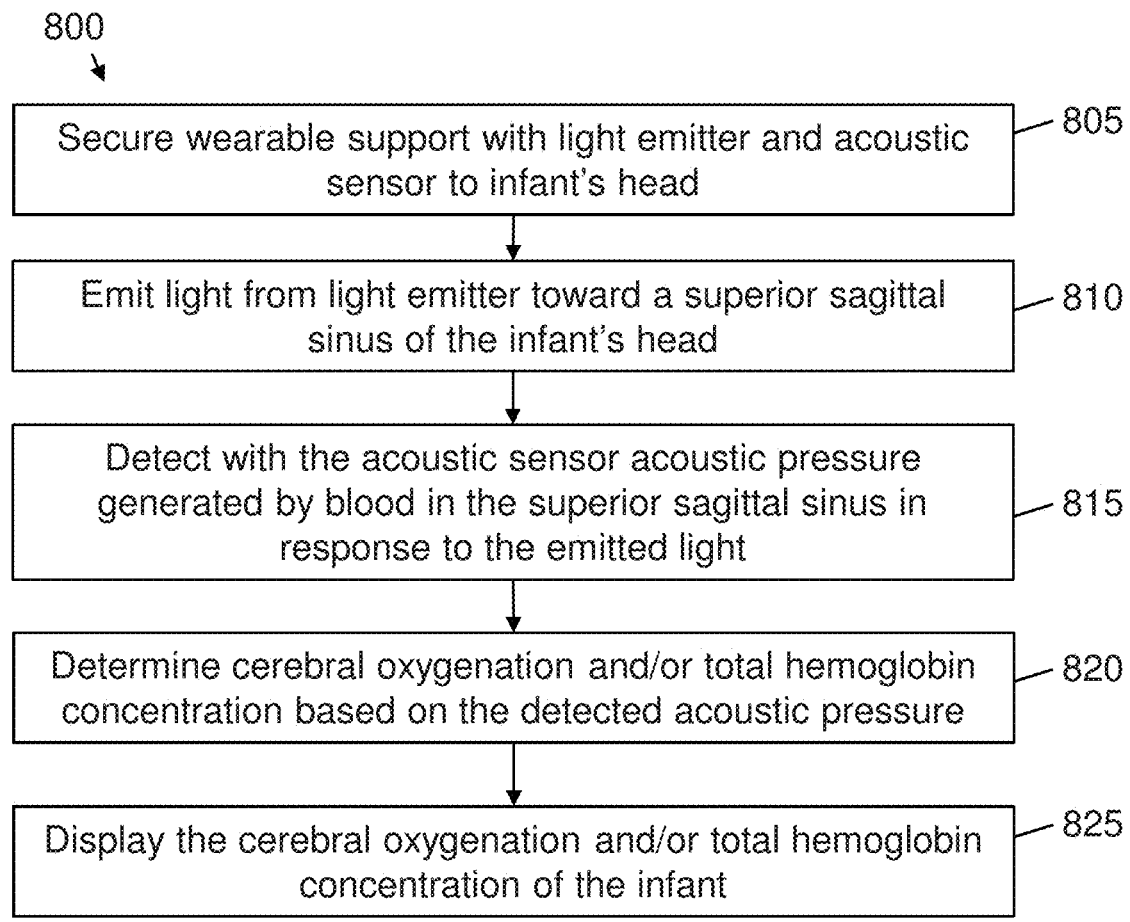
FIG. 8 shows a flowchart of a method for optoacoustic monitoring of cerebral oxygenation of an infant, according to many embodiments.

FIG. 8 shows a flowchart of a method 800 for optoacoustic monitoring of cerebral oxygenation and/or total hemoglobin concentration of an infant.

In step 805, a wearable support is secured the infant's head, wherein the wearable support comprises a light emitter and an acoustic sensor as described herein. For example, the wearable support may comprise a headband, a head cap, and/or a pillow as described, having the light emitter and the acoustic sensor integrated therein.

Securing the wearable support to the infant's head may comprise positioning the light emitter to a first predetermined position relative to the infant's head, such that the light emitter emits light toward a superior sagittal sinus of the infant's head. For example, the first predetermined position may comprise a posterior portion of the infant's head, such as the posterior fontanelle, or a superior portion of the infant's head, such as the anterior fontanelle. Securing the wearable support to the infant's head may further comprise positioning the acoustic sensor to a second predetermined position relative to the infant's head, such that the acoustic sensor can detect the acoustic pressure generated by blood in the superior sagittal sinus in response to the light. For example, the second predetermined position may comprise an anterior portion of the infant's head, such as the forehead, a superior portion of the infant's head, such as the anterior fontanelle, or a posterior portion of the infant's head, such as the posterior fontanelle. The first predetermined position and the second position may be different and substantially opposite one another for transmission mode measurements. Alternatively, the first predetermined position and the second predetermined position may be substantially the same position or adjacent positions in close proximity to one another for reflection mode measurements.

In step 810, the light emitter emits light toward the superior sagittal sinus (SSS) of the infant's head. Light of one or more wavelengths may be emitted towards the SSS, such as any wavelength within a range from about 600 nm to about 1100 nm. A plurality of light pulses of different wavelengths may be sequentially emitted towards the SSS, as described herein.

In step 815, the acoustic sensor detects the acoustic pressure generated by blood in the SSS in response to the emitted light. The acoustic sensor may be configured to receive pressure waves and convert the pressure waves into electrical signals. The electrical signals may be transmitted to a processor communicatively coupled to the acoustic sensor.

In step 820, the cerebral oxygenation and/or total hemoglobin concentration of the infant is determined based on the detected acoustic pressure. This step may be performed by a processor communicatively coupled to the acoustic sensor, configured to apply one or more algorithms as described herein to the signals received from the acoustic sensor to determine one or more parameters of cerebral oxygenation (e.g., total hemoglobin concentration and/or saturation).

In step 825, the cerebral oxygenation and/or total hemoglobin concentration of the infant may be displayed to a user of the optoacoustic system. For example, the optoacoustic signal and/or the total hemoglobin concentration and saturation may be displayed via a monitor communicatively coupled to the processor configured to perform step 820. The display may be updated at predetermined time intervals to provide continuous, substantially real-time monitoring of cerebral oxygenation of the infant.

Although the above steps show the method 800 of monitoring cerebral oxygenation and/or total hemoglobin concentration in an infant using an optoacoustic system in accordance with many embodiments, a person of ordinary skill in the art will recognize many variations based on the teachings described herein. The steps may be completed in a different order. Steps may be added or deleted. Some of the steps may comprise sub-steps. Many of the steps may be repeated as often as beneficial to the measurement(s).

One or more of the steps of the method 800 may be performed with various circuitry, as described herein, for example one or more of the processor, controller, or circuit board described above and herein. Such circuitry may be programmed to provide one or more steps of the method 800, and the program may comprise program instructions stored on a computer readable memory or programmed steps of the logic circuitry such as programmable array logic or a field programmable gate array, for example.

Aspects of the present disclosure also include methods of measuring oxygenation. Such methods include the application of formulas to measure oxygenation when signals are good (i.e., there is low background). Exemplary formulas to determine blood oxygenation at different wavelengths of light signals are listed below, where R is the ratio of optoacoustic amplitudes, for instance, at 760 and 800 nm ($R=A_{760}/A_{800}$):

$$760 \text{ nm: } SO_2=1.54-0.76\cdot R \rightarrow R=2.02-1.31\cdot SO_2$$

Similar formulas are valid for other wavelengths, for instance 850 nm:

$$850 \text{ nm: } SO_2=-2.42+2.66\cdot R \rightarrow R=0.91+0.38\cdot SO_2$$

In general, for any wavelength: $R=a_i+b_i\cdot SO_2$

For instance, introducing 1.0 to generate a difference of signals would yield:

$$R-1 = a_i' + b_i' \cdot SO_2 - 1$$

$$\frac{A_{760}}{A_{800}} - 1 = a'_i + b'_i \cdot SO_2 - 1$$

And, the differential signal $D_{760}=A_{760}-A_{800}$ may be represented by the equation:

$$\frac{A_{760} - A_{800}}{A_{800}} =$$
$$b'_i \cdot SO_2 + a'_i - 1 = -1.31 \cdot SO_2 + 2.02 - 1 = -1.31 \cdot SO_2 + 1.02$$

So, in general, for any wavelength, the below equation (Eq. 1) may apply:

$$\frac{A_i - A_{800}}{A_{800}} = b'_i \cdot SO_2 + a'_i - 1$$

And, a third wavelength (e.g. 850 nm) may be introduced to remove $A_{800}$ as follows with the following equation (Eq. 2):

$$\frac{A_{850} - A_{800}}{A_{800}} = 0.38 \cdot SO_2 + 0.91 - 1 = 0.38 \cdot SO_2 - 0.09$$

To remove $A_{800}$, Eq. 1 may be divided by Eq. 2 as follows.

$$RDS = \frac{A_{760} - A_{800}}{A_{850} - A_{800}} = \frac{-1.31 \cdot SO_2 + 1.02}{0.38 \cdot SO_2 - 0.09}$$
$$(0.38 \cdot SO_2 - 0.09) \cdot (A_{760} - A_{800}) = (-1.31 \cdot SO_2 + 1.02) \cdot (A_{850} - A_{800})$$

And where $D_{760}=A_{760}-A_{800}$ and $D_{850}=A_{850}-A_{800}$:

$$0.38 \cdot D_{760} \cdot SO_2 - 0.09 \cdot D_{760} = -1.31 \cdot D_{850} \cdot SO_2 + 1.02 \cdot D_{850}$$
$$0.38 \cdot D_{760} \cdot SO_2 + 1.31 \cdot D_{850} \cdot SO_2 = 1.02 \cdot D_{850} + 0.09 \cdot D_{760}$$
$$SO_2(0.38 \cdot D_{760} + 1.31 \cdot D_{850}) = 1.02 \cdot D_{850} + 0.09 \cdot D_{760}$$
$$SO_2 = \frac{1.02 \cdot D_{850} + 0.09 \cdot D_{760}}{0.38 \cdot D_{760} + 1.31 \cdot D_{850}}$$

The last above equation for $SO_2$ can be used to measure oxygenation using any (bad or good) signals with high background from hair or skin melanin. Therefore, three or more wavelengths of light or two or more wavelength pairs for light may be used to measure oxygenation optoacoustically, even in conditions of high background. The wavelengths noted above are examples only, and other wavelengths are also contemplated for use as described above and herein. The above coefficients for the various formulas and equations are examples only as well, and other coefficients for the above formulas and equations are also contemplated for use, for example, as described in U.S. patent application Ser. No. 14/794,022, filed Jul. 8, 2015, which is incorporated herein by reference.

Experimental Data

Figure 9A:
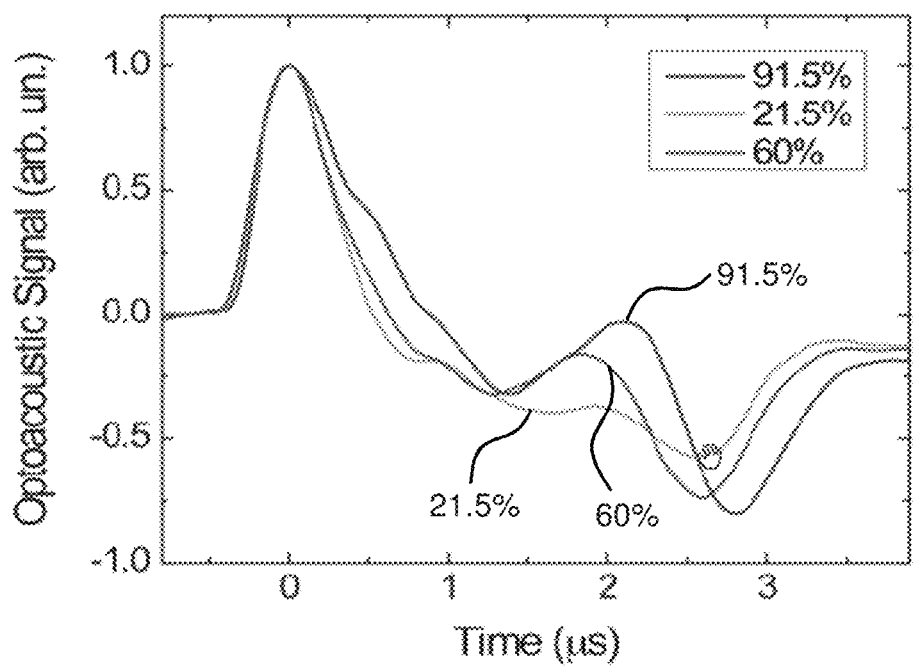
FIG. 9A is a graph showing typical optoacoustic signals recorded at 1064 nm from sheep SSS at different levels of $SSS(SO_2)$, according to many embodiments.
Figure 9B:
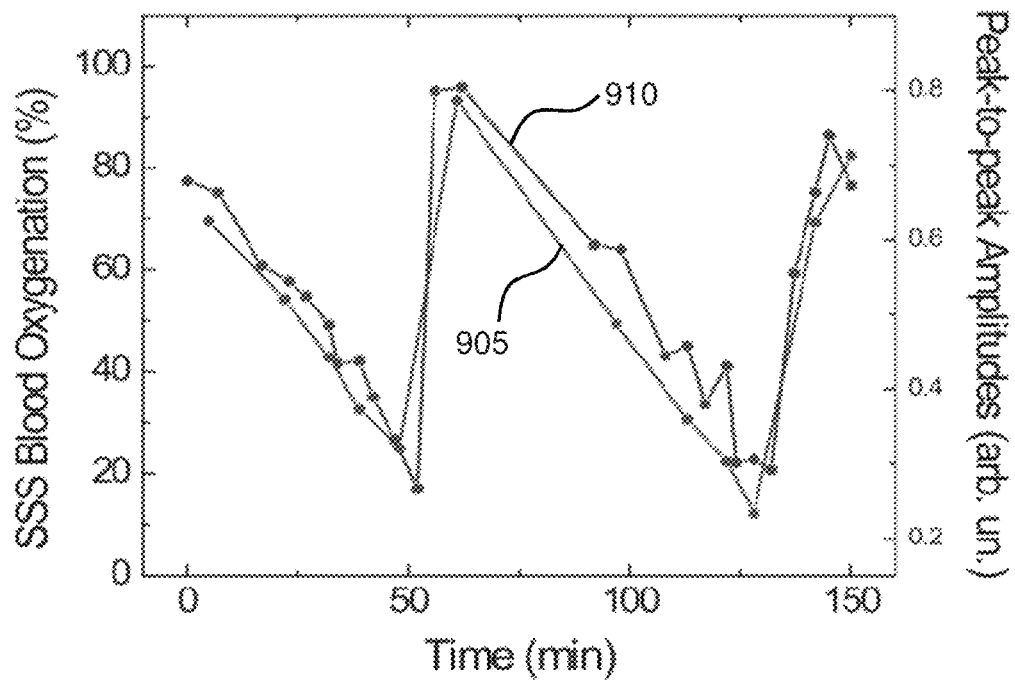
FIG. 9B is a graph demonstrating changes in the peak-to-peak amplitude of the optoacoustic signal during two cycles of variation of blood oxygenation, according to many embodiments.

FIGS. 9A and 9B show results of a study performed in adult sheep using an optoacoustic monitoring system as described herein. In an experimental procedure, an optical parametric oscillator (OPO)-based optoacoustic system as described herein was used to determine $SSS(SO_2)$ in 8 anesthetized adult sheep (weight 35-40 kg). In adult sheep the SSS (diameter=2-3 mm) is similar in size to that of human neonates and the sheep skull thickness (5-6 mm) is thicker and more optically and acoustically dense than the soft tissue overlying the neonatal SSS (3-4 mm). The measurements derived using the optoacoustic system were compared to measurements obtained using invasive hemoximetry (CO-Oximetry), which is generally considered the gold standard for oxygenation measurements. A catheter was inserted through a small craniotomy into the SSS to permit direct blood sampling for measurement in a CO-Oximeter, and the CO-Oximeter measurements were compared to simultaneously recorded optoacoustic signals. To produce a wide range of $SSS(SO_2)$ for in vivo validation, $PaCO_2$ was altered from 20 to 40 mmHg (to increase cerebral blood flow), and $FiO_2$ values were altered from 0.07 to 0.21. The probe was scanned laterally over the skull to identify the peak signal, which for all sheep was within 2 mm of the midline.

FIG. 9A shows typical optoacoustic signals recorded at 1064 nm from sheep SSS at different levels of $SSS(SO_2)$ (91.5%, 21.5%, and 60%). The first peak (at t=0 μs) is induced in the skull, while the second peak (t=2 μs) is induced in the SSS due to absorption of light by blood. FIG. 9B demonstrates changes in the peak-to-peak amplitude of the optoacoustic signal 905 during two cycles of variation of blood oxygenation. As expected, the amplitudes paralleled those of the CO-Oximeter signals 910, representing directly measured $SSS(SO_2)$. For example, the amplitude of the peak at 1064 nm directly varied with hemoglobin saturation (data shown in FIG. 9B); in comparison, the amplitude of the peak at 700 nm inversely varied with saturation (data not shown). Bland-Altman analysis demonstrated high agreement between optoacoustically predicted $SSS(SO_2)$ and directly measured $SSS(SO_2)$. The results demonstrate that the optoacoustic technique provides accurate, quantitative, noninvasive measurement of $SSS(SO_2)$.

Figure 10A:
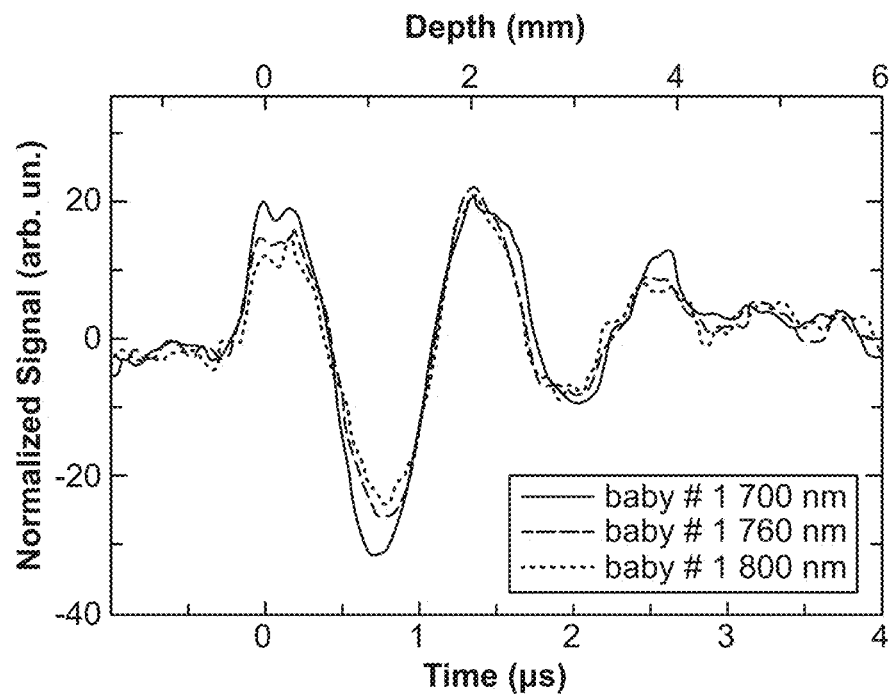
FIG. 10A is a graph that plots optoacoustic signals recorded from the superior sagittal sinus (SSS) of a first baby at various wavelengths, according to many embodiments.
Figure 10B:
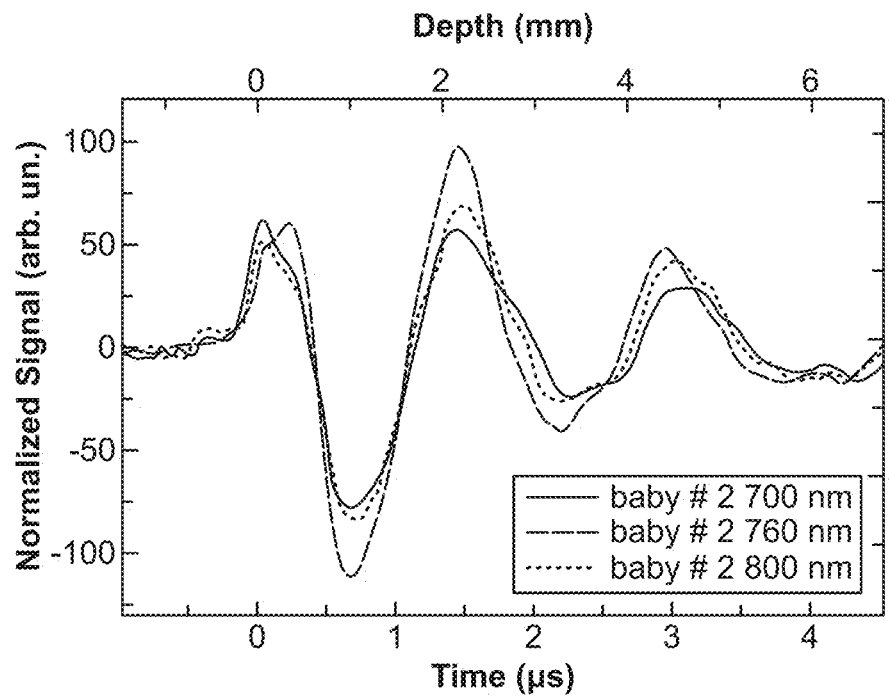
FIG. 10B is a graph that plots typical optoacoustic signals recorded from the SSS of a second baby at various wavelengths, according to many embodiments.

FIGS. 10A and 10B show results of a study performed in hemodynamically stable neonates using an optoacoustic monitoring system as described herein. In another experimental procedure, hemodynamically stable neonates were optoacoustically measured in order to simulate optoacoustic monitoring. An optical parametric oscillator (OPO) was controlled by a personal computer that was programmed to rapidly switch between three wavelengths: 800 nm (isobestic point), 760 nm, and 700 nm at an energy level of 15 microjoules, similar to the energy produced by pulsed laser diodes. $SSS(SO_2)$ was then calculated from each of two pairs of wavelengths (760 nm and 800 nm) and (700 nm and 800 nm) and then the mean of the two calculations was determined. By taking the mean of two or more calculations, a more accurate measurement of blood oxygenation can be made.

FIGS. 10A and 10B show the raw data from which $SSS(SO_2)$ was calculated for Babies 1 and 2. In the first of two neonates (Baby 1: weight 1,795 g; current weight 2,885 g; gestational age 32 wks), at two time intervals, $SSS(SO_2)$ was 58% and 69%. In the second neonate (Baby 2: weight 3,040 g; gestational age 39 wks), at three time intervals, $SSS(SO_2)$ was 55%, 60%, and 62%. These measurements are consistent with the expected ranges and with physiologic changes over time. While measurements at three different wavelengths were taken in the study, it is noted that measurements can be taken at any numbers of wavelengths. For example, in some embodiments, measurements can be taken at 760 nm and 800 nm. Furthermore, while the optoacoustic probe described herein comprises an optical waveguide that turns light generated by a light source through 90°, it is noted that the light can be emitted from the probe at any angle from 0° (straight from the tip of the probe) to 90°. The particular angle that is used may depend upon which angle provides the easiest access to the neonatal head and fontanelle depending upon neonatal head position and anatomy.

FIGS. 11A-14B show results of additional studies performed in hemodynamically stable neonates using an optoacoustic monitoring system as described herein. The optoacoustic system was used to take both single and continuous measurements of SSS blood oxygenation in normal, low birth weight, and very low birth weight infants. The system used either a multi-wavelength optical parametric oscillator (OPO) or laser diodes as a laser light source, operating in the spectral range from 680 to 1064 nm. The system included an optoacoustic probe comprising a light emitter and acoustic detector as described herein, such as a fiber-optic light delivery system and a wide-band ultrasound transducer. The optoacoustic system was controlled by a personal computer that was programmed to rapidly switch between wavelengths in the spectral range from 700 to 1064 nm. Most preferable wavelengths for oxygenation measurements were 760 nm and 800 nm (the isobestic point). The probe was scanned over the SSS of subjects to obtain best signals from the SSS. An algorithm was developed to provide real-time and continuous measurement of oxygenation in blood vessels including the SSS, the algorithm utilizing differences in absorption spectra of oxy- and deoxyhemoglobin. The system included a processor in communication with the probe and configured with instructions to perform fast data acquisition and processing, and display in real time the current absolute value of blood oxygenation as well as continuous oxygenation values vs. time.

Figure 11A:
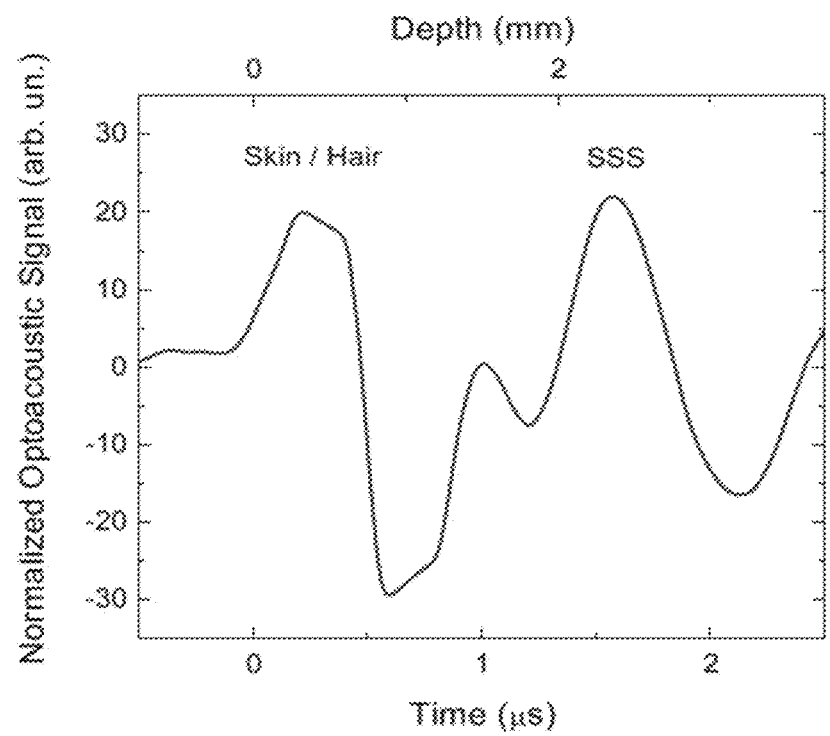
FIG. 11A is a graph representing a normalized optoacoustic signal from the SSS of an infant, recorded using an optoacoustic system as described herein, according to many embodiments.
Figure 11B:
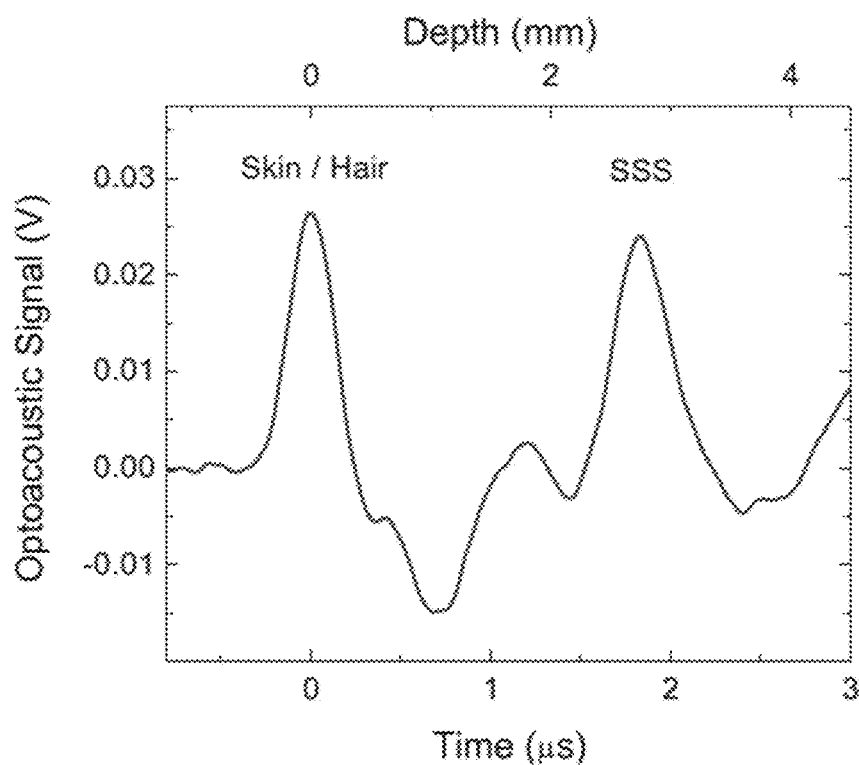
FIG. 11B is a graph presenting an optoacoustic signal from the SSS of an infant, recorded using an optoacoustic system as described herein, according to many embodiments.

FIG. 11A represents a normalized optoacoustic signal from the SSS and the overlying tissues obtained with the OPO-based optoacoustic system, from a low birth weight infant (2,025 g). The first peak in the optoacoustic signal (at a time of about 0 μs) was induced in the skin and hair, while the second peak (at a time of about 1.5 μs) was induced in the SSS. The upper X-axis represents depth (in mm) from the skin surface calculated by multiplying the time scale (the lower X-axis, in μs) by the speed of sound in soft tissue (1.5 mm/μs). The SSS depth calculated using the signal was approximately 2.3 mm. FIG. 11B represents an optoacoustic signal from the SSS and the overlying tissues obtained with the laser diode-based optoacoustic system, from a normal weight infant (2,615 g). The first peak in the optoacoustic signal (at a time of about 0 μs) was induced in the skin and hair, while the second peak (at a time of about 1.9 μs) was induced in the SSS. The SSS depth calculated using the signal was approximately 2.9 mm.

Figure 12A:
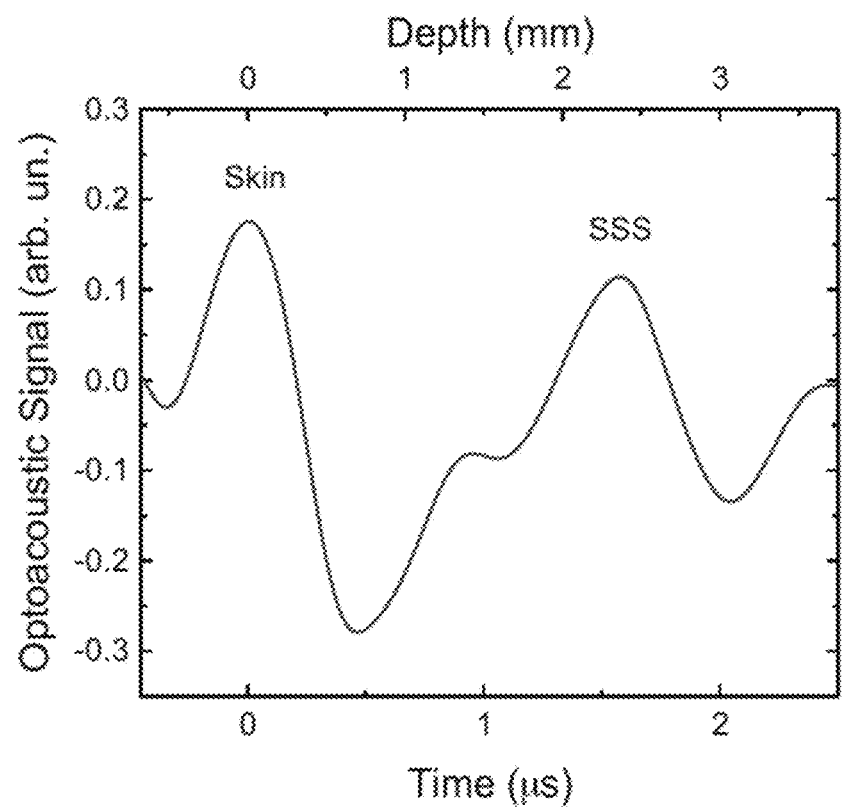
FIG. 12A is a graph showing a typical optoacoustic signal from the SSS of an infant, recorded using an optoacoustic system in the reflection mode as described herein, according to many embodiments.
Figure 12B:
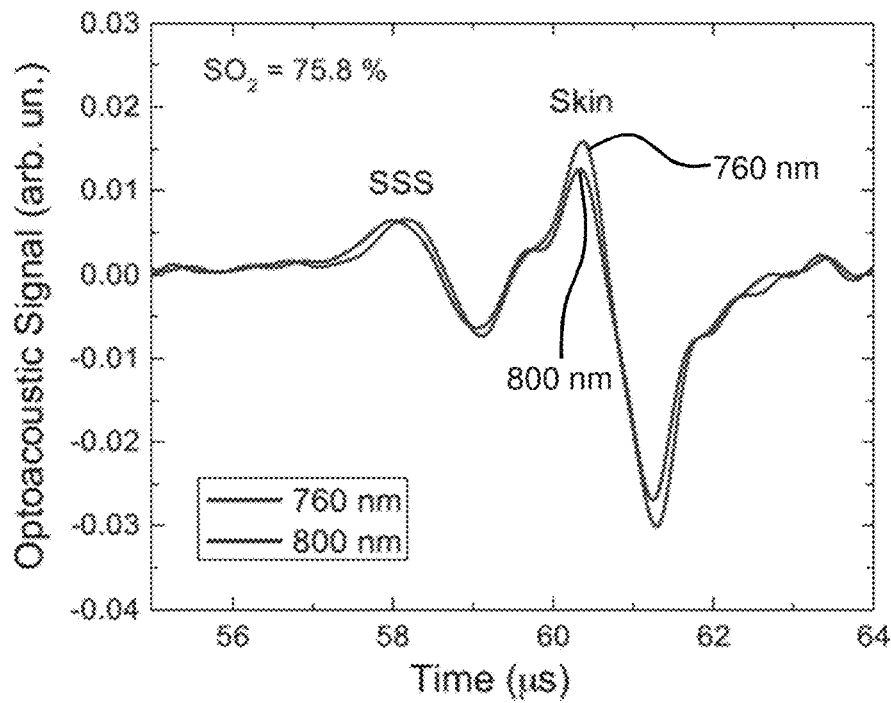
FIG. 12B is a graph showing a typical optoacoustic signal from the SSS of an infant, recorded using an optoacoustic system in the transmission mode as described herein, according to many embodiments.

FIGS. 12A and 12B show typical optoacoustic signals recorded using an OPO-based optoacoustic system in different measurement modes as described herein. The optoacoustic system was used to measure the subject's head in either the transmission mode or the reflection mode as described herein. Reflection mode measurements were made either through the anterior fontanelle (e.g., as shown in FIGS. 7A and 7B) or through the posterior fontanelle (e.g., as shown in FIGS. 6A and 6B). Transmission mode measurements were made by irradiating the head from one side such as the inion area to target the SSS (or the confluence of sinuses), and detecting ultrasound signals from the other side of the head such as the forehead (e.g., as shown in FIGS. 2A-5B).

FIG. 12A shows a typical optoacoustic signal recorded from the SSS of a premature very low birth weight infant (weight 1,020 g; gestational age 27 wks) at 800 nm, in the reflection mode. The first peak (at t=0 μs) is induced in the skin, while the second peak (at t=1.6 μs) is induced in the infant's SSS at a depth of 2.4 mm. FIG. 12B shows a typical optoacoustic signal recorded from the SSS of a premature very low birth weight infant (985 g) at 760 nm and 800 nm, in the transmission mode. The first peak (at 58 μs) is induced in the SSS and arrives to the transducer earlier than the peak from the skin (at 60 μs). This is because the SSS is closer to the transducer than the skin surface. By contrast, in reflection mode measurements, as shown in FIG. 12A, the first peak is induced in the skin and the second peak is induced in the SSS, since the skin surface is closer to the transducer than the SSS. The transmission mode allows for accurate measurements of the SSS peak parameters (amplitude and slope), because the SSS peak is the first arriving signal and therefore there is little or no interfering ringing in the transducer that can potentially reduce the accuracy of the measurements in the reflection mode. The measurements at two wavelengths, 760 nm and 800 nm, allow for calculation of the SSS blood oxygenation with high accuracy (75.8% for the particular infant whose data are shown in FIG. 12B). The exponential slope of the SSS peak can be used to measure total hemoglobin concentration (THb) in neonates, using the equations as described herein. For the data shown in FIG. 12B, the calculated THb, based on the slope of the signal measured at 800 nm, was 10.8 g/dL. This number is in good agreement with the actual THb of 10.2 g/dL, measured invasively using blood sampling from the neonate.

Figure 13A:
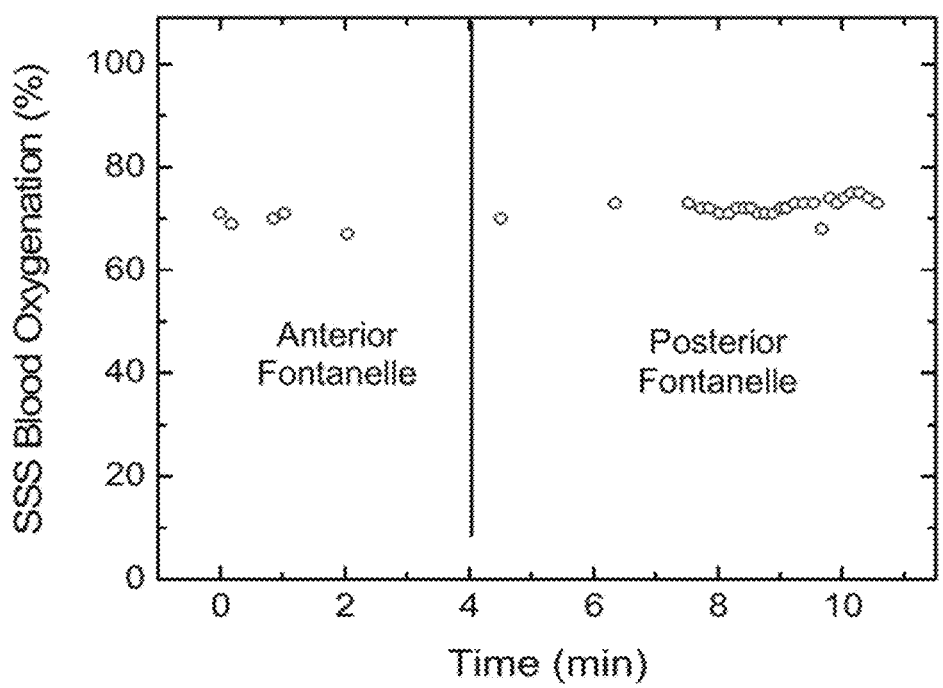
FIGS. 13A and 13B are graphs showing the continuous, real-time monitoring of SSS blood oxygenation in low birth weight infants, using an optoacoustic system as described herein, according to many embodiments.
Figure 13B:
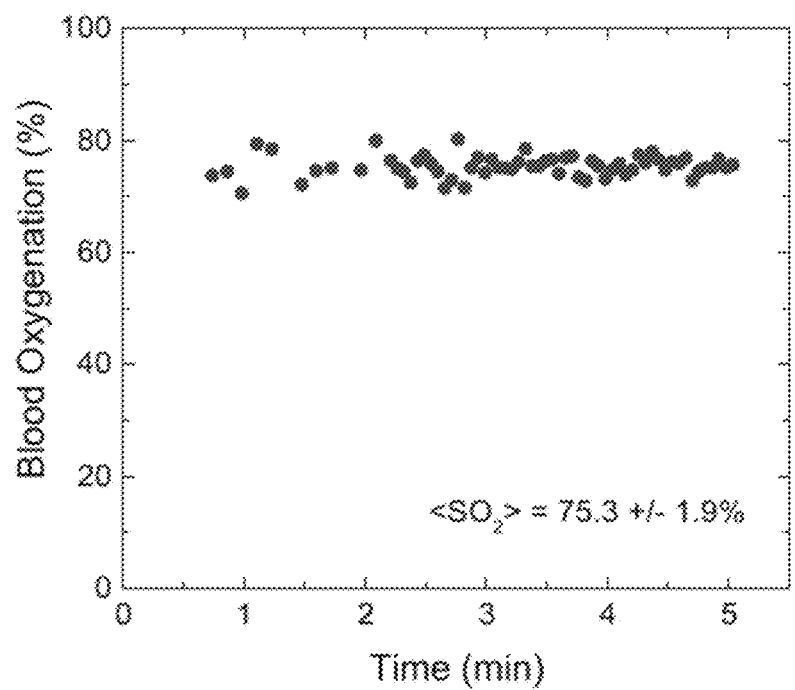

FIGS. 13A and 13B show the continuous, real-time monitoring of SSS blood oxygenation in low birth weight infants, using the optoacoustic monitoring system as described herein. FIG. 13A shows data from a premature infant with very low birth weight of 675 g. The measurements with the optoacoustic system were performed every 2 minutes or every 10 seconds. First, the measurements were conducted through the anterior fontanelle (data shown on left side of graph). Then the optoacoustic probe was applied on the posterior fontanelle (data shown on right side of graph). The measurements from the both sites yielded similar results. The average SSS blood oxygenation and standard deviation were 72.0% and 1.7%, respectively. It should be noted that the standard deviation includes natural variation of the SSS blood oxygenation, precision of the system, and errors associated with motion artifacts. FIG. 13B shows data from a premature, very low birth weight infant (1,040 g) using an OPO-based optoacoustic system. Up to the second minute (t=2 min), each data point was obtained by signal averaging for 10 seconds. After the second minute, each data point was obtained by signal averaging for 2.5 seconds, which reduced motion artifacts. The average SSS blood oxygenation and standard deviation were 75.3% and 1.9%, respectively.

Figure 14A:
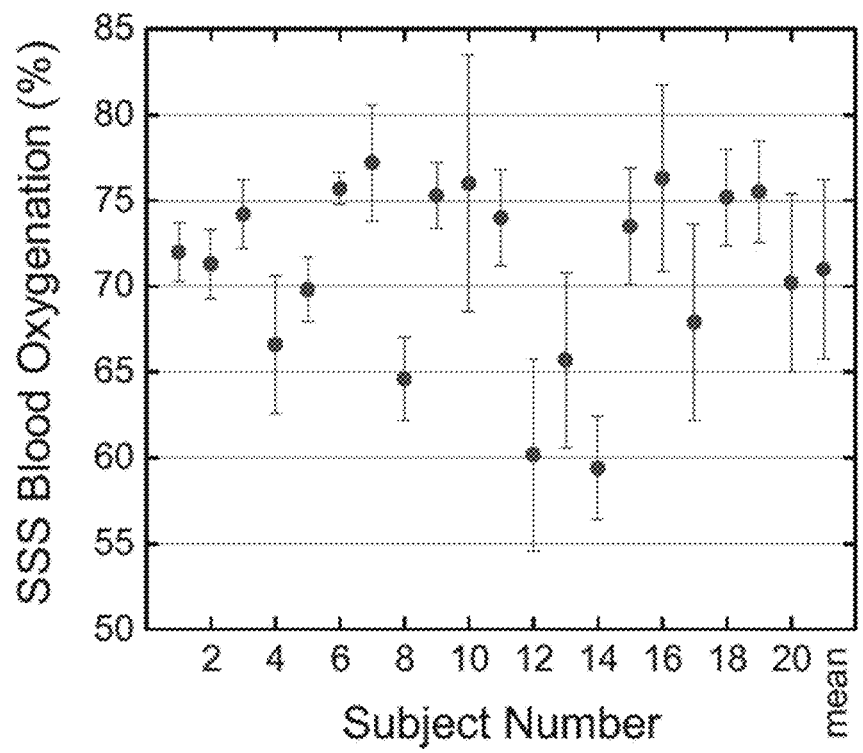
FIGS. 14A and 14B are graphs demonstrating the monitoring of SSS($SO_2$) over time in 18 low birth weight and very low birth weight neonates, according to many embodiments.
Figure 14B:
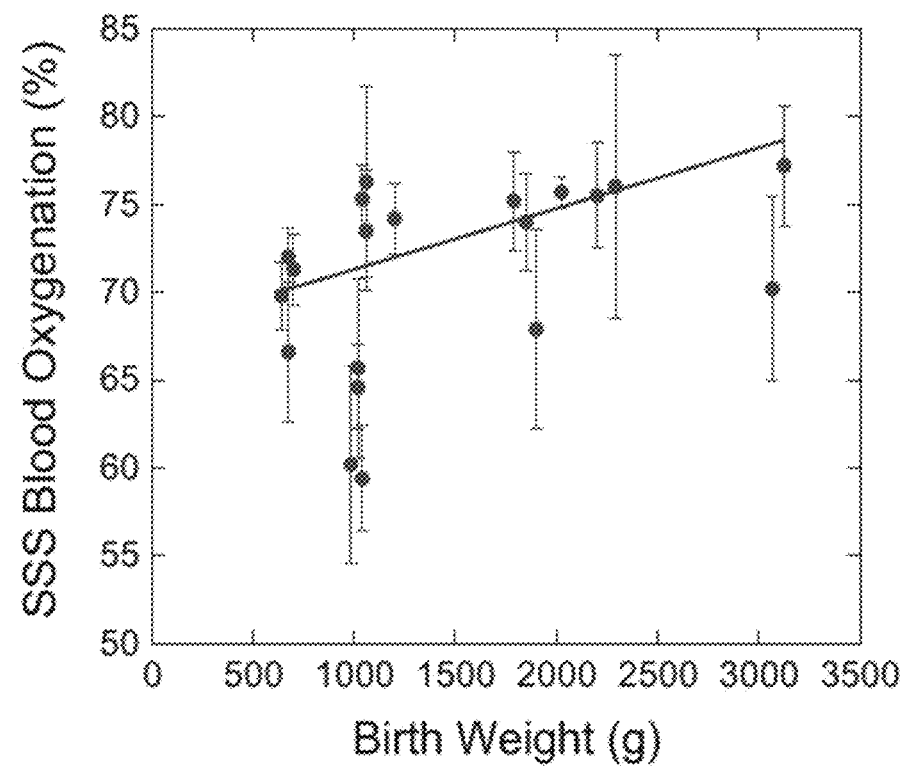

FIGS. 14A and 14B demonstrate the monitoring of SSS ($SO_2$) over time in 18 low birth weight and very low birth weight neonates. An OPO-based optoacoustic system was used to measure SSS($SO_2$) in both the reflection mode and transmission mode. In 2 of the 18 subjects, two studies were performed in each of the 2 subjects, resulting in a combined total of 20 studies. The means and standard deviations shown on the graph represent data from each study. The final data point (at the far right of the graph) represents the mean of the combined data from all studies. The data of FIG. 14A suggest that the normal range of SSS($SO_2$) in hemodynamically stable preterm infants is approximately 55-85%. FIG. 14B shows SSS blood oxygenation vs. birth weight in hemodynamically stable low birth weight and very low birth weight neonates. The data shows a weak positive correlation between birth weight and SSS blood oxygenation ($r^2$=0.27).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for monitoring one or more of cerebral oxygenation or total hemoglobin concentration of an infant, the method comprising:
   emitting light from a light emitter secured to a head of the infant with a wearable support secured onto the infant's head, wherein the wearable support is sized and configured to cover at least a portion of the infant's head to be secured thereto, and wherein the light emitter is positioned on the wearable support so the light emitter faces and emits light toward a superior sagittal sinus of the infant's head through a fontanelle;
   detecting, with an acoustic sensor secured to the infant's head with the wearable support, acoustic pressure generated by blood in the superior sagittal sinus in response to the emitted light, wherein the acoustic sensor is positioned on the wearable support to one or more of an anterior portion or a posterior portion of the infant's head to detect the acoustic pressure generated by blood in the superior sagittal sinus through the fontanelle; and
   determining, with a processor in communication with the light emitter and the acoustic sensor, the one or more of cerebral blood oxygenation or total hemoglobin concentration in response to the detected acoustic pressure.

2. The method of claim 1, wherein emitting the light comprises emitting the light from a posterior portion of the infant's head, and wherein detecting the acoustic pressure comprises detecting the acoustic pressure from the posterior portion of the infant's head.

3. The method of claim 1, wherein emitting the light comprises emitting the light from a superior portion of the infant's head, and wherein detecting the acoustic pressure comprises detecting the acoustic pressure from the superior portion of the infant's head.

4. The method of claim 1, wherein determining cerebral oxygenation comprises determining venous oxygenation.

5. A method for monitoring one or more of cerebral oxygenation or total hemoglobin concentration of an infant, the method comprising:
   (A) securing a wearable support onto a head of the infant, the wearable support being sized and configured to cover at least a portion of the infant's head to be secured thereto, wherein securing the wearable support comprises:
      (i) positioning a light emitter coupled to the wearable support so that the light emitter faces and emits light toward a superior sagittal sinus of the infant's head through a fontanelle, and
      (ii) positioning an acoustic sensor coupled to the wearable support so that the acoustic sensor faces the superior sagittal sinus to detect acoustic pressure generated by blood therein through the fontanelle when the superior sagittal sinus blood absorbs the light;
   (B) causing the light to be emitted and the acoustic pressure to be detected; and
   (C) determining, with the aid of a processor in communication with the light emitter and the acoustic sensor, cerebral oxygenation in response to the detected acoustic pressure.

6. The method of claim 5, wherein the light is emitted from a posterior portion of the infant's head, and wherein the acoustic pressure is detected from the posterior portion of the infant's head.

7. The method of claim 5, wherein the light is emitted from a superior portion of the infant's head, and wherein the acoustic pressure is detected from the superior portion of the infant's head.

8. The method of claim 5, wherein determining cerebral oxygenation comprises determining venous oxygenation.

9. A cerebral oxygenation monitoring apparatus comprising:
   a wearable support sized and configured to cover at least a portion of a head of an infant to be secured thereto, the wearable support comprising a posterior portion configured to be placed over a posterior portion of the infant's head when the wearable support is secured to the head of the infant and a superior portion configured to be placed over a superior portion of the infant's head when the wearable support is secured to the head of the infant;
   a light emitter positioned on the posterior portion of the wearable support so that the light emitter faces and emits toward a superior sagittal sinus of the infant's head through a fontanelle when the wearable support is secured onto the infant's head; and
   an acoustic sensor positioned on the superior portion of the wearable support so that the acoustic sensor faces the superior portion of the head of the infant to detect acoustic pressure generated by blood in the superior sagittal sinus through the fontanelle when the superior sagittal sinus blood absorbs the light,
   wherein cerebral blood oxygenation is determined in response to the acoustic pressure detected by the acoustic sensor.

10. The apparatus of claim 9, further comprising a processor configured to determine one or more of cerebral venous oxygenation or total hemoglobin concentration in response to the detected acoustic pressure.

11. The apparatus of claim 9, wherein the wearable support comprises one or more of a head band, a pillow with the headband extending from the pillow, or a head cap.

12. The apparatus of claim 11, wherein the wearable support comprises the headcap and the head cap comprises a central band adapted to form a continuous loop around the infant's head.

13. The apparatus of claim 12, wherein the head cap further comprises a sagittal band extending between front and back sides of the central band to form a path across a top of the infant's head, and wherein the light emitter and the acoustic sensor are positioned on the sagittal band.

14. The apparatus of claim 12, wherein the head cap further comprises a web extending upward and rearward from the central band to wrap around a rear of the infant's head above the central band, and wherein the light emitter and the acoustic sensor are positioned on the central band.

15. The apparatus of claim 12, wherein the head cap is configured to cover the entirety of the infant's head superior to the central band.

16. A cerebral oxygenation monitoring apparatus comprising:
a wearable support sized and configured to cover at least a portion of a head of an infant to be secured thereto, the wearable support comprising a posterior portion configured to be placed over a posterior portion of the infant's head when the wearable support is secured to the head of the infant and a superior portion configured to be placed over a superior portion of the infant's head when the wearable support is secured to the head of the infant;
a light emitter positioned on the superior portion of the wearable support so that the light emitter faces and emits light toward a superior sagittal sinus of the infant's head through a fontanelle when the wearable support is secured onto the infant's head; an acoustic sensor positioned on the posterior portion of the wearable support so that the acoustic sensor faces the posterior portion of the head of the infant to detect acoustic pressure generated by blood in the superior sagittal sinus through the fontanelle when the superior sagittal sinus blood absorbs the light,
wherein cerebral blood oxygenation is determined in response to the acoustic pressure detected by the acoustic sensor.

17. The apparatus of claim 16, further comprising a processor configured to determine one or more of cerebral venous oxygenation or total hemoglobin concentration in response to the detected acoustic pressure.

18. The apparatus of claim 16, wherein the wearable support comprises one or more of a head band, a pillow with the headband extending from the pillow, or a head cap.

19. The apparatus of claim 18, wherein the head cap comprises a central band adapted to form a continuous loop around the infant's head.

20. The apparatus of claim 19, wherein the head cap further comprises a sagittal band extending between front and back sides of the central band to form a path across a top of the infant's head, and wherein the light emitter and the acoustic sensor are positioned on the sagittal band.

21. The apparatus of claim 19, wherein the head cap further comprises a web extending upward and rearward from the central band to wrap around a rear of the infant's head above the central band, and wherein the light emitter and the acoustic sensor are positioned on the central band.

22. The apparatus of claim 19, wherein the head cap is configured to cover the entirety of the infant's head superior to the central band.

23. A cerebral oxygenation monitoring apparatus comprising:
a wearable support sized and configured to cover at least a portion of a head of an infant to be secured thereto, the wearable support comprising a posterior portion configured to be placed over a posterior portion of the infant's head when the wearable support is secured to the head of the infant;
a light emitter positioned on the posterior portion of the wearable support so that the light emitter faces and emits toward a superior sagittal sinus of the infant's head through a fontanelle when the wearable support is secured onto the infant's head; and
an acoustic sensor position on the posterior portion of the wearable support so that the acoustic sensor faces the posterior portion of the head of the infant to detect acoustic pressure generated by blood in the superior sagittal sinus through the fontanelle when the superior sagittal sinus blood absorbs the light,
wherein cerebral blood oxygenation is determined in response to the acoustic pressure detected by the acoustic sensor.

24. The apparatus of claim 23, further comprising a processor configured to determine one or more of cerebral venous oxygenation or total hemoglobin concentration in response to the detected acoustic pressure.

25. The apparatus of claim 23, wherein the wearable support comprises one or more of a head band, a pillow with the headband extending from the pillow, or a head cap.

26. The apparatus of claim 25, wherein the wearable support comprises the headcap and the head cap comprises a central band adapted to form a continuous loop around the infant's head.

27. The apparatus of claim 26, wherein the head cap further comprises a sagittal band extending between front and back sides of the central band to form a path across a top of the infant's head, and wherein the light emitter and the acoustic sensor are positioned on the sagittal band.

28. The apparatus of claim 26, wherein the head cap further comprises a web extending upward and rearward from the central band to wrap around a rear of the infant's head above the central band, and wherein the light emitter and the acoustic sensor are positioned on the central band.

29. The apparatus of claim 23, wherein the head cap is configured to cover the entirety of the infant's head superior to the central band.

30. A cerebral oxygenation monitoring apparatus comprising:
a wearable support sized and configured to cover at least a portion of a head of an infant to be secured thereto, the wearable support comprising a superior portion configured to be placed over a superior portion of the infant's head when the wearable support is secured to the head of the infant;
a light emitter positioned on the superior portion of the wearable support so that the light emitter faces and emits toward the superior portion of the infant's head through a fontanelle when the wearable support is secured onto the infant's head; and
an acoustic sensor position on the superior portion of the wearable support so that the acoustic sensor faces the superior portion of the head of the infant to detect acoustic pressure generated by blood in the superior sagittal sinus through the fontanelle when the superior sagittal sinus blood absorbs the light,
wherein cerebral blood oxygenation is determined in response to the acoustic pressure detected by the acoustic sensor.

31. The apparatus of claim 30, further comprising a processor configured to determine one or more of cerebral venous oxygenation or total hemoglobin concentration in response to the detected acoustic pressure.

32. The apparatus of claim 30, wherein the wearable support comprises one or more of a head band, a pillow with the headband extending from the pillow, or a head cap.

33. The apparatus of claim 32, wherein the wearable support comprises the headcap and the head cap comprises a central band adapted to form a continuous loop around the infant's head.

34. The apparatus of claim 33, wherein the head cap further comprises a sagittal band extending between front and back sides of the central band to form a path across a top of the infant's head, and wherein the light emitter and the acoustic sensor are positioned on the sagittal band.

35. The apparatus of claim 33, wherein the head cap further comprises a web extending upward and rearward from the central band to wrap around a rear of the infant's head above the central band, and wherein the light emitter and the acoustic sensor are positioned on the central band.

36. The apparatus of claim 33, wherein the head cap is configured to cover the entirety of the infant's head superior to the central band.

37. A neonatal cerebral oxygenation monitoring apparatus comprising:
- a wearable support sized and configured to cover at least a portion of a head of an infant to be secured thereto, the wearable support comprising a posterior portion configured to be placed over a posterior portion of the infant's head when the wearable support is secured to the head of the infant and a superior portion configured to be placed over a superior portion of the infant's head when the wearable support is secured to the head of the infant;
- a light emitter positioned on the posterior portion of the wearable support so that the light emitter faces and emits toward a superior sagittal sinus of the infant's head when the wearable support is secured onto the infant's head; and
- an acoustic sensor positioned on the superior portion of the wearable support so that the acoustic sensor faces the superior portion of the head of the infant to detect acoustic pressure generated by blood in the superior sagittal sinus when the superior sagittal sinus blood absorbs the light,
- wherein the light emitter is configured to emit the light through a posterior fontanelle of the infant's head,
- wherein the acoustic sensor is configured to detect the acoustic pressure through an anterior fontanelle of the infant's head, and
- wherein cerebral blood oxygenation is determined in response to the acoustic pressure detected by the acoustic sensor.

38. The apparatus of claim 37, further comprising a processor configured to determine one or more of cerebral venous oxygenation or total hemoglobin concentration in response to the detected acoustic pressure.

39. The apparatus of claim 37, wherein the wearable support comprises one or more of a head band, a pillow with the headband extending thereform, or a head cap.

40. The apparatus of claim 39, wherein the wearable support comprises the headcap and the head cap comprises a central band adapted to form a continuous loop around the infant's head.

41. The apparatus of claim 40, wherein the head cap further comprises a sagittal band extending between front and back sides of the central band to form a path across a top of the infant's head, and wherein the light emitter and the acoustic sensor are positioned on the sagittal band.

42. The apparatus of claim 40, wherein the head cap further comprises a web extending upward and rearward from the central band to wrap around a rear of the infant's head above the central band, and wherein the light emitter and the acoustic sensor are positioned on the central band.

43. The apparatus of claim 40, wherein the head cap is configured to cover the entirety of the infant's head superior to the central band.

44. A neonatal cerebral oxygenation monitoring apparatus comprising:
- a wearable support sized and configured to cover at least a portion of a head of an infant to be secured thereto, the wearable support comprising a posterior portion configured to be placed over a posterior portion of the infant's head when the wearable support is secured to the head of the infant and a superior portion configured to be placed over a superior portion of the infant's head when the wearable support is secured to the head of the infant;
- a light emitter positioned on the superior portion of the wearable support so that the light emitter faces and emits light toward a superior sagittal sinus of the infant's head when the wearable support is secured onto the infant's head;
- an acoustic sensor positioned on the posterior portion of the wearable support so that the acoustic sensor faces the posterior portion of the head of the infant to detect acoustic pressure generated by blood in the superior sagittal sinus when the superior sagittal sinus blood absorbs the light,
- wherein the light emitter is configured to emit the light through an anterior fontanelle of the infant's head,
- wherein the acoustic sensor is configured to detect the acoustic pressure through a posterior fontanelle of the infant's head, and
- wherein cerebral blood oxygenation is determined in response to the acoustic pressure detected by the acoustic sensor.

45. The apparatus of claim 44, further comprising a processor configured to determine one or more of cerebral venous oxygenation or total hemoglobin concentration in response to the detected acoustic pressure.

46. The apparatus of claim 44, wherein the wearable support comprises one or more of a head band, a pillow with the headband extending thereform, or a head cap.

47. The apparatus of claim 46, wherein the wearable support comprises the headcap and the head cap comprises a central band adapted to form a continuous loop around the infant's head.

48. The apparatus of claim 47, wherein the head cap further comprises a sagittal band extending between front and back sides of the central band to form a path across a top of the infant's head, and wherein the light emitter and the acoustic sensor are positioned on the sagittal band.

49. The apparatus of claim 47, wherein the head cap further comprises a web extending upward and rearward from the central band to wrap around a rear of the infant's head above the central band, and wherein the light emitter and the acoustic sensor are positioned on the central band.

50. The apparatus of claim 47, wherein the head cap is configured to cover the entirety of the infant's head superior to the central band.

* * * * *